US012575779B2

(12) United States Patent
Kenttä et al.

(10) Patent No.: US 12,575,779 B2
(45) Date of Patent: Mar. 17, 2026

(54) TECHNIQUES FOR DETECTING ATRIAL FIBRILLATION

(71) Applicant: Oura Health Oy, Oulu (FI)

(72) Inventors: Tuomas Viljami Kenttä, Liminka (FI); Steve Kent, San Francisco, CA (US); Xi Zhang, Daly City, CA (US)

(73) Assignee: Oura Health Oy, Oulu (FI)

( * ) Notice: Subject to any disclaimer, the term of this patent is extended or adjusted under 35 U.S.C. 154(b) by 398 days.

(21) Appl. No.: 17/984,870

(22) Filed: Nov. 10, 2022

(65) Prior Publication Data

US 2023/0165508 A1 Jun. 1, 2023

Related U.S. Application Data

(60) Provisional application No. 63/283,889, filed on Nov. 29, 2021.

(51) Int. Cl.
| | |
|---|---|
| *A61B 5/361* | (2021.01) |
| *A61B 5/00* | (2006.01) |
| *A61B 5/024* | (2006.01) |
| *G16H 50/30* | (2018.01) |

(52) U.S. Cl.
CPC .......... *A61B 5/361* (2021.01); *A61B 5/02427* (2013.01); *A61B 5/6802* (2013.01); *A61B 5/7275* (2013.01); *A61B 5/7435* (2013.01); *G16H 50/30* (2018.01)

(58) Field of Classification Search
CPC ... A61B 5/361; A61B 5/02427; A61B 5/6802; A61B 5/7275; A61B 5/7435; G16H 50/30
See application file for complete search history.

(56) References Cited

U.S. PATENT DOCUMENTS

| | | | | |
|---|---|---|---|---|
| 10,398,381 B1 * | 9/2019 | Heneghan | ............ | A61B 5/6824 |
| 10,709,339 B1 * | 7/2020 | Lusted | .................. | A61B 5/282 |
| 2015/0342478 A1 * | 12/2015 | Galen | .................. | A61B 5/726 |
| | | | | 600/479 |
| 2016/0166161 A1 * | 6/2016 | Yang | .................. | A61B 5/02427 |
| | | | | 600/476 |
| 2018/0249962 A1 * | 9/2018 | Koivisto | ................ | H03F 3/187 |

(Continued)

FOREIGN PATENT DOCUMENTS

| | | | | | |
|---|---|---|---|---|---|
| WO | WO-2011048592 A1 * | 4/2011 | | ........... | A61B 5/0059 |
| WO | WO-2016123216 A1 * | 8/2016 | | ........... | A44C 9/0053 |
| WO | WO-2021233319 A1 * | 11/2021 | | ........... | A61B 5/0004 |

*Primary Examiner* — Unsu Jung
*Assistant Examiner* — Laura Hodge
(74) *Attorney, Agent, or Firm* — Holland & Hart LLP

(57) ABSTRACT

Methods, systems, and devices for atrial fibrillation (AFib) detection are described. A method may include acquiring physiological data collected from a user via a wearable ring device, the physiological data including temperature data and motion data, and identifying that a measurement trigger condition for AFib has been satisfied based on the temperature data satisfying a temperature threshold and the motion data satisfying a motion threshold. The method may include sampling photoplethysmogram (PPG) data for the user via the wearable ring device based on identifying satisfaction of the measurement trigger condition, and classifying one or more AFib states based on the sampled PPG data. The method may further include causing a GUI of a user device to display an indication of the one or more AFib states.

20 Claims, 14 Drawing Sheets

(56) References Cited

U.S. PATENT DOCUMENTS

| 2020/0100693 | A1* | 4/2020 | Velo | ..................... | G16H 50/20 |
| 2021/0379388 | A1* | 12/2021 | Connor | .............. | A61M 60/232 |
| 2022/0117556 | A1* | 4/2022 | Kranck | ................. | A61B 5/681 |

* cited by examiner

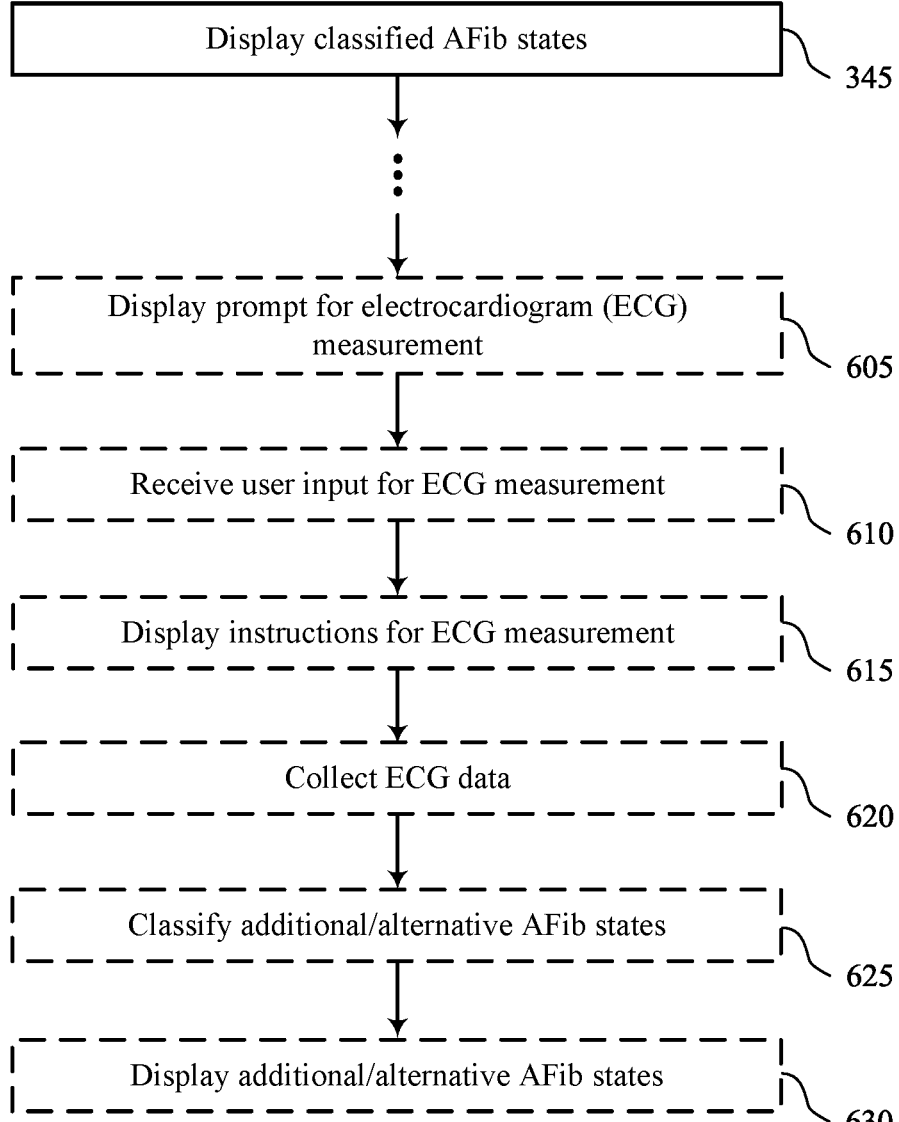
FIG. 6

Conductive Metal
Frame 820

Inner Housing
805

Electrode 815

Outer Housing
810

104

800

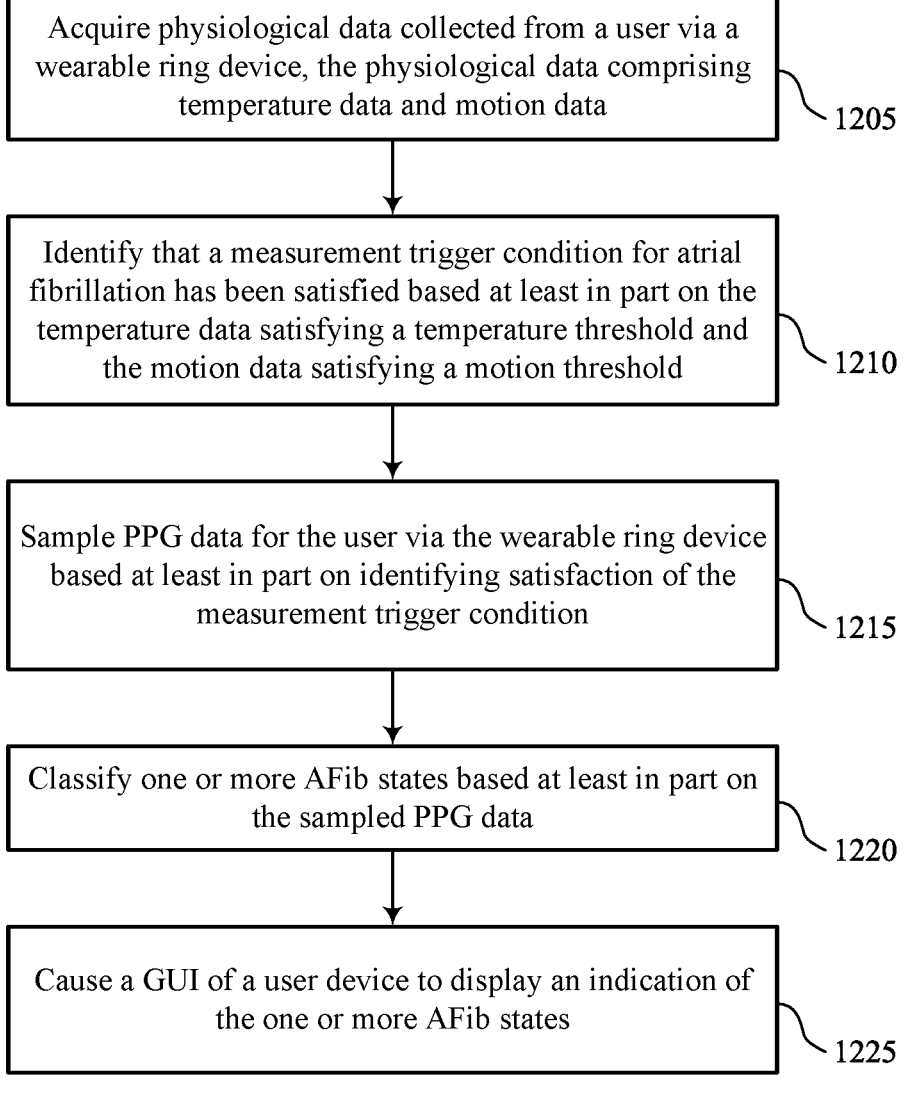

Acquire physiological data collected from a user via a wearable ring device, the physiological data comprising temperature data and motion data

1205

Identify that a measurement trigger condition for atrial fibrillation has been satisfied based at least in part on the temperature data satisfying a temperature threshold and the motion data satisfying a motion threshold

1210

Sample PPG data for the user via the wearable ring device based at least in part on identifying satisfaction of the measurement trigger condition

1215

Classify one or more AFib states based at least in part on the sampled PPG data

1220

Cause a GUI of a user device to display an indication of the one or more AFib states

TECHNIQUES FOR DETECTING ATRIAL FIBRILLATION

CROSS REFERENCE

The present Application for Patent claims the benefit of U.S. Provisional Patent Application No. 63/283,889 by KENTTÄ et al., entitled "TECHNIQUES FOR DETECTING ATRIAL FIBRILLATION," filed Nov. 29, 2021, assigned to the assignee hereof, and expressly incorporated by reference herein.

FIELD OF TECHNOLOGY

The following relates to wearable devices and data processing, including techniques for detecting atrial fibrillation (AFib).

BACKGROUND

Some wearable devices may be configured to collect physiological data from users, including temperature data, heart rate data, and the like. Many users have a desire for more insight regarding their physical health.

BRIEF DESCRIPTION OF THE DRAWINGS

FIGS. 3 through 6 illustrate examples of process flows that support techniques for detecting AFib in accordance with aspects of the present disclosure.

FIGS. 12 through 14 show flowcharts illustrating methods that support techniques for detecting AFib in accordance with aspects of the present disclosure.

DETAILED DESCRIPTION

Figure 1:
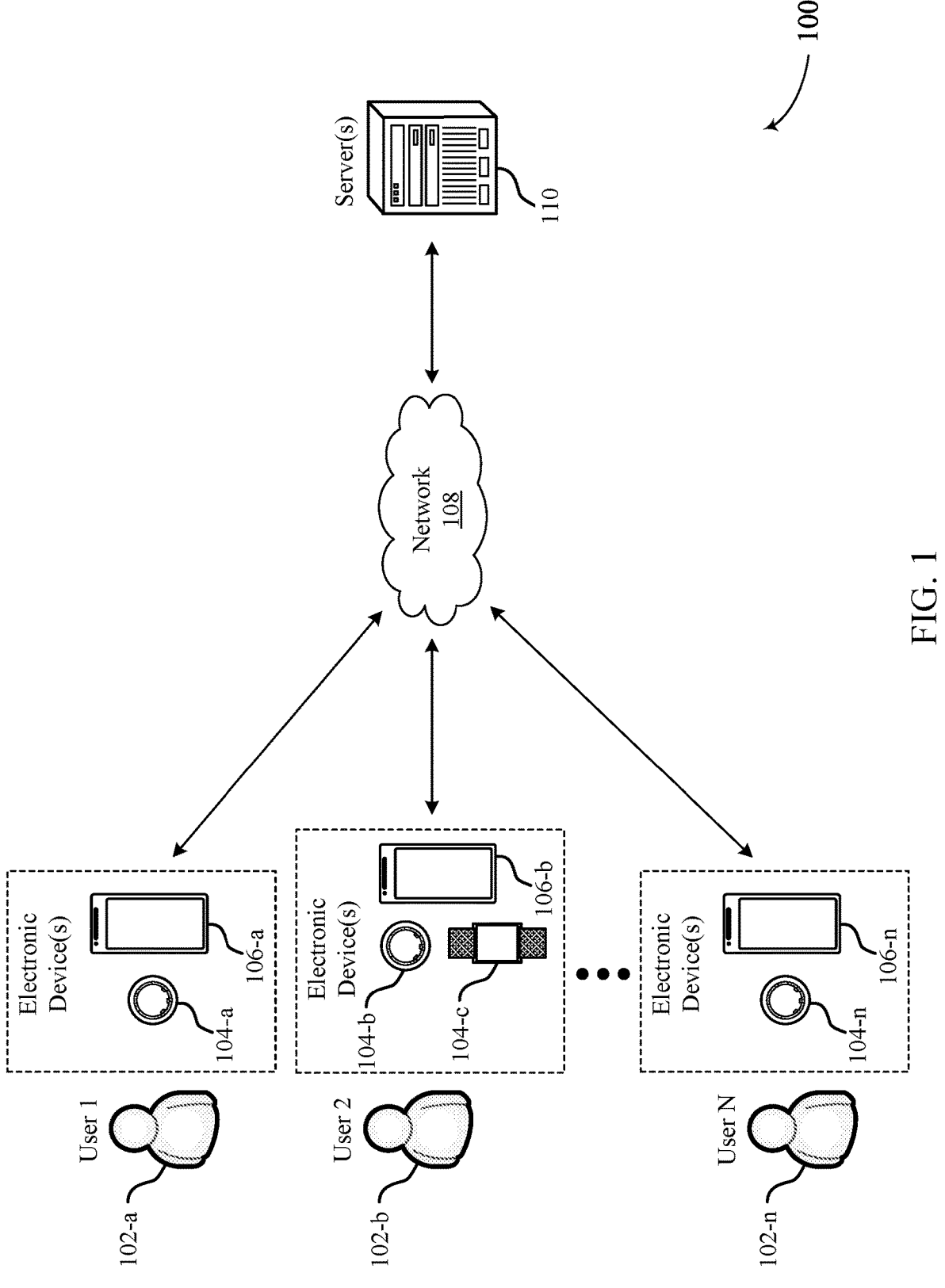
FIG. 1 illustrates an example of a system that supports techniques for detecting AFib in accordance with aspects of the present disclosure.

Some wearable devices may be configured to collect physiological data from users, including temperature data, heart rate data, and the like. Many users have a desire for more insight regarding their physical health. Physiological data collected from users may be used to detect and monitor potential health conditions, such as atrial fibrillation (AFib). AFib is the most common sustained cardiac arrhythmia, affecting roughly 1-2% of the general population, and is a major risk factor for several cardiovascular conditions, including stroke. The hallmark of AFib is an irregular heartbeat that is sometimes referred to as an "irregularly irregular" heart beat. This irregular electrical activity resulting from AFib generates seemingly random sequences of heart beats with increased inter-beat interval (IBI) variability and altered photoplethysmogram (PPG) signal morphology that may be distinguished from normal sinus rhythm.

Over 33 million people worldwide suffer from AFib, an irregular heart beat that can lead to blood clots, stroke, heart failure, and death. AFib is the most common rhythm disorder with clinical significance, and is becoming more prevalent worldwide, driven by poor lifestyle factors (e.g., inactivity, poor sleep, diet, stress). Furthermore, medical costs are substantially higher in AFib patients than medically matched control patients, due to more frequent hospitalization and mortality. Further, AFib may be intermittent and may not be accompanied by other symptoms, meaning that AFib is often asymptomatic. As such, AFib can be difficult to diagnose, and many cases go undetected until complications occur.

Normally, electrocardiogram (ECG) measurements are used to detect arrhythmias, including arrhythmias associated with AFib. The paroxysmal nature of AFib in its initial course renders AFib diagnosis challenging, and requires long-term monitoring to capture AFib episodes. However, many individuals do not receive regular ECG readings, meaning that ECG readings provide a very limited view into an individual's overall health at the time the ECG reading is performed. Sometimes implantable devices can be used to record the electrical activity of the heart in an attempt to detect abnormal heart rhythms that cannot be caught by long-term ECG recordings or event monitors. However, implantable devices may require invasive surgical procedures. Further, devices that are configured to detect AFib may acquire physiological data from a user at a time that is not likely to yield accurate AFib results. As such, current techniques for monitoring and diagnosing AFib are deficient.

Accordingly, aspects of the present disclosure are directed to the use of wearable devices to monitor physiological data for a user and detect AFib. In particular, aspects of the present disclosure are directed to a system including a wearable ring device that is configured to utilize infrared PPG sensors to identify and differentiate normal sinus rhythm from AFib using detection algorithms. For example, a wearable ring device described herein may acquire physiological data from a user when one or more AFib measurement trigger conditions are satisfied. Collecting data upon the satisfaction of AFib measurement trigger conditions may help ensure that acquired physiological data will result in accurate AFib detection. Subsequently, the system may perform PPG sampling, and may classify one or more AFib states for the user based on the sampled PPG data. The classified AFib states may then be presented to the user in order to provide the user with a more complete picture of their overall health, and enable them to make lifestyle changes to prevent and reduce AFib occurrences.

Some aspects of the present disclosure are directed to techniques for an AFib "spot check" including a wearable device that samples PPG data for AFib classification according to a regular periodicity, an irregular periodicity, in response to a user input, or any combination thereof. By introducing on-demand AFib spot-check, techniques described herein may enable users to regularly check on their heart rhythm that may improve AFib detection. Further, wearable devices described herein may be configured to periodically or aperiodically perform PPG measurements for AFib classification (e.g., automatic AFib spot-check). Such techniques enable a more comprehensive view of a user's heart rhythm that may allow for improved AFib detection. In particular, AFib detection techniques described herein may enable earlier detection of AFib, and may provide a user with peace of mind if they are experiencing symptoms such as palpitations.

Aspects of the present disclosure may utilize physiological data collected from a user (e.g., PPG data) to classify one or more AFib states associated with the user. Classified AFib states may be used to evaluate a relative AFib risk level for the user. Classified AFib states may include, but are not limited to, a positive AFib state, a negative AFib state, a potential AFib state, an inconclusive AFib state, and the like. Additional or alternative AFib states may also be used.

Classified AFib states may then be displayed/presented to the user along with messaging that provides more information associated with the respective AFib state. For example, upon detecting a potential/possible AFib state, a user device described herein may present a message to the user that reads: "Possible AFib detected: You may wish to confirm this with a clinician or run a 12-lead ECG to check for other possible abnormalities." By way of another example, upon detecting a negative AFib state, a user device described herein may present a message to the user that reads: "Normal: Your heart rate and rhythm are normal with no or very few abnormal beats." Comparatively, upon detecting an inconclusive AFib state, a user device may display messages that read "Unclassified: The algorithm was not able to classify your heartbeat as AFib or normal," or "Unreadable: The recording was not readable due to interference. Try to relax and hold still for a better measurement; rest your arms or move to a quiet location. Ensure your ring is placed correctly and the sensors are clean."

Aspects of the present disclosure may provide users with a more comprehensive picture of their overall health, including their risk for AFib. In addition to improving AFib monitoring and detection, techniques described herein may be used to provide tailored guidance to a user that is aimed to reduce the user's risk for AFib episodes. It has been found that the majority of triggers for AFib, such as excess caffeine or alcohol, exercise, psychological anxiety and insufficient sleep, are modifiable behaviors. As such, techniques described herein may facilitate both AFib detection as well as secondary prevention or reduction in the frequency and severity of AFib by providing guidance that may facilitate lifestyle modification. In contrast, existing therapies for AFib may carry risk of severe bleeding or involve invasive surgical procedures (e.g., ablation) that scar the heart. As such, AFib detection and prevention techniques described herein may provide a less invasive and proactive option for users who are prone to AFib.

In some aspects, techniques described herein may enable users to "tag" events or subjective feelings to help improve the identification and prevention of AFib triggers for each respective user. For example, users may be able to tag or input the use of potential "triggers" (e.g., alcohol, caffeine, poor sleep, anxiety episodes) via a user device. In such cases, AFib detection algorithms described herein may identify potential triggers for AFib episodes for each respective user based on inputted tags and collected physiological data, and may algorithmically determine the likelihood that a trigger is followed by an AFib episode, as well as predict a severity or duration of an AFib episode. Such techniques may be used to provide personalized coaching and guidance for each user, that may improve strategies for the management of anxiety, alcohol, caffeine, and other modifiable AFib triggers linked with poor sleep and vagal tone (e.g., low heart rate variability (HRV)).

Aspects of the disclosure are initially described in the context of systems supporting physiological data collection from users via wearable devices. Additional aspects of the disclosure are described in the context of example process flows, AFib detection procedures, wearable ring devices, and GUIs that support AFib detection. Aspects of the disclosure are further illustrated by and described with reference to apparatus diagrams, system diagrams, and flowcharts that relate to techniques for detecting AFib.

FIG. 1 illustrates an example of a system 100 that supports techniques for detecting AFib in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/ all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some that may measure physiological parameters and some that may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time when a user 102 is asleep, and classify periods of time when the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time when the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5)

multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for AFib detection and prevention. In particular, a wearable device 104 of the system 100 (e.g., wearable ring device 104) may be configured to utilize infrared PPG sensors to identify and differentiate normal sinus rhythm from AFib using detection algorithms.

For example, a wearable ring device 104 of the system 100 may acquire physiological data from a user 102 when one or more AFib measurement trigger conditions are satisfied. Collecting data upon the satisfaction of AFib measurement trigger conditions may help ensure that acquired physiological data will result in accurate AFib detection. Measurement trigger conditions may include when the user is substantially still (e.g., motion below a threshold), and when the user's skin temperature is high (e.g., temperature above a threshold). Subsequently, the system may perform PPG sampling, and may classify one or more AFib states for the user 102 based on the sampled PPG data. Classified AFib states may include, but are not limited to, a positive AFib state, a negative AFib state, a potential AFib state, an inconclusive AFib state, and the like. The classified AFib states may then be presented to the user 102 via a user device 106 in order to provide the user 102 with a more complete picture of their overall health, and enable them to make lifestyle changes to prevent and reduce AFib occurrences.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
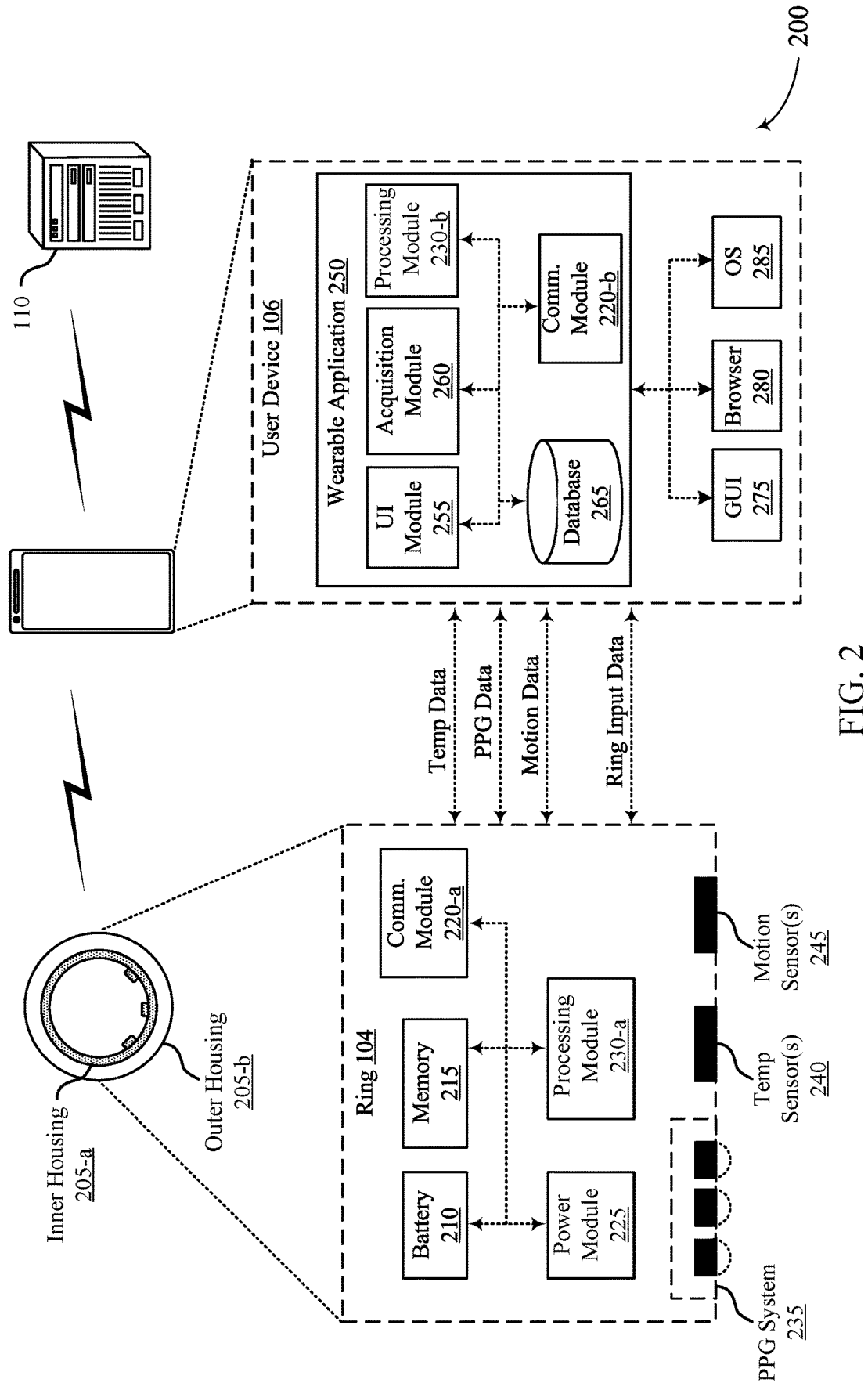
FIG. 2 illustrates an example of a system that supports techniques for detecting AFib in accordance with aspects of the present disclosure.

FIG. 2 illustrates an example of a system 200 that supports techniques for detecting AFib in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-a. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106 and the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate that may be stored in memory 215 and may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 and the optical receiver(s) receive transmitted light that is reflected through the region of the user's finger. In some implementations, the PPG system 235 may be configured as a transmissive PPG system 235 and the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS 285), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., a Sleep Score, a Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time when the respective users typically sleep.

In some implementations, each overall score for a user for each respective day (e.g., a Sleep Score, a Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the respective devices of the system 200 may support techniques for AFib detection and prevention. In particular, the wearable device 104 of the system 200 (e.g., wearable ring device 104) may be configured to utilize the PPG system 235 to identify and differentiate normal sinus rhythm from AFib using detection algorithms.

For example, a wearable ring device 104 of the system 100 may acquire physiological data from a user 102 when one or more AFib measurement trigger conditions are satisfied. Collecting data upon the satisfaction of AFib measurement trigger conditions may help ensure that acquired physiological data will result in accurate AFib detection. Subsequently, the system may perform PPG sampling, and may classify one or more AFib states for the user 102 based on the sampled PPG data. Classified AFib states may include, but are not limited to, a positive AFib state, a negative AFib state, a potential AFib state, an inconclusive AFib state, and the like. The classified AFib states may then be presented to the user 102 via a user device 106 in order to provide the user 102 with a more complete picture of their overall health, and enable them to make lifestyle changes to prevent and reduce AFib occurrences.

For example, as will be described in further detail herein, the system 200 may be configured to identify potential "triggers" for AFib for each respective user, such as anxiety, alcohol, caffeine, and poor sleep (e.g., based on "tags" input by the user). In such cases, the system may provide guidance to the user to increase a frequency or relative timing of such "triggers" in order to influence lifestyle changes to prevent and reduce AFib occurrences (e.g., "It looks like caffeine late at night may increase your chances of AFib occurrences. You should consider reducing your caffeine consumption after noon.").

The various devices of the system 200 may support an AFib "spot check," and the wearable device 104 samples PPG data for AFib classification according to a regular periodicity, an irregular periodicity, in response to a user input, or any combination thereof. For example, in some cases, a user may input a request for an AFib spot check via the GUI 275, and the system 200 may sample PPG data for AFib detection in response to the request. By introducing on-demand AFib spot-check, techniques described herein may enable users to regularly check on their heart rhythm that may improve AFib detection. Further, wearable devices described herein may be configured to periodically or aperiodically perform PPG measurements for AFib classification (e.g., automatic AFib spot-check). Such techniques enable a more comprehensive view of a user's heart rhythm that may allow for improved AFib detection.

In some cases, classified AFib states may be used to selectively adjust one or more parameters associated with AFib measurement, such as a periodicity of AFib measurement, a power level provided to components used for AFib measurement (e.g., power level provided to PPG system 235), and the like. Moreover, in some aspects, classified AFib states may be used to trigger or prompt ECG measurements for a user. For example, upon presenting a positive or potential AFib measurement to a user, the system 200 may prompt the user to perform an ECG measurement. In such cases, the system 200 may provide instructions to the user that assist the user with performing an ECG measurement using the wearable ring device 104 (e.g., instructions for how to position the ring in order to perform an ECG measurement). As such, techniques described herein may utilize PPG data to perform a preliminary AFib diagnosis, and may prompt a user to perform ECG measurements that may be used to more accurately perform AFib diagnosis based on classified AFib states.

As noted previously herein, the blood vessels in the finger (e.g., arteries, capillaries) are more accessible via LEDs as compared to blood vessels in the wrist, that may lead to higher quality PPG signals and other physiological data. The higher quality PPG data, along with the improved ease of capturing physiological data during sleep with the ring form factor, may provide more efficient and accurate AFib detection. In particular, the higher quality data combined with continuous physiological data collection may enable earlier AFib detection as compared to other wearable devices.

AFib detection and prevention techniques described herein may be further shown and described with reference to FIG. 3.

Figure 3:
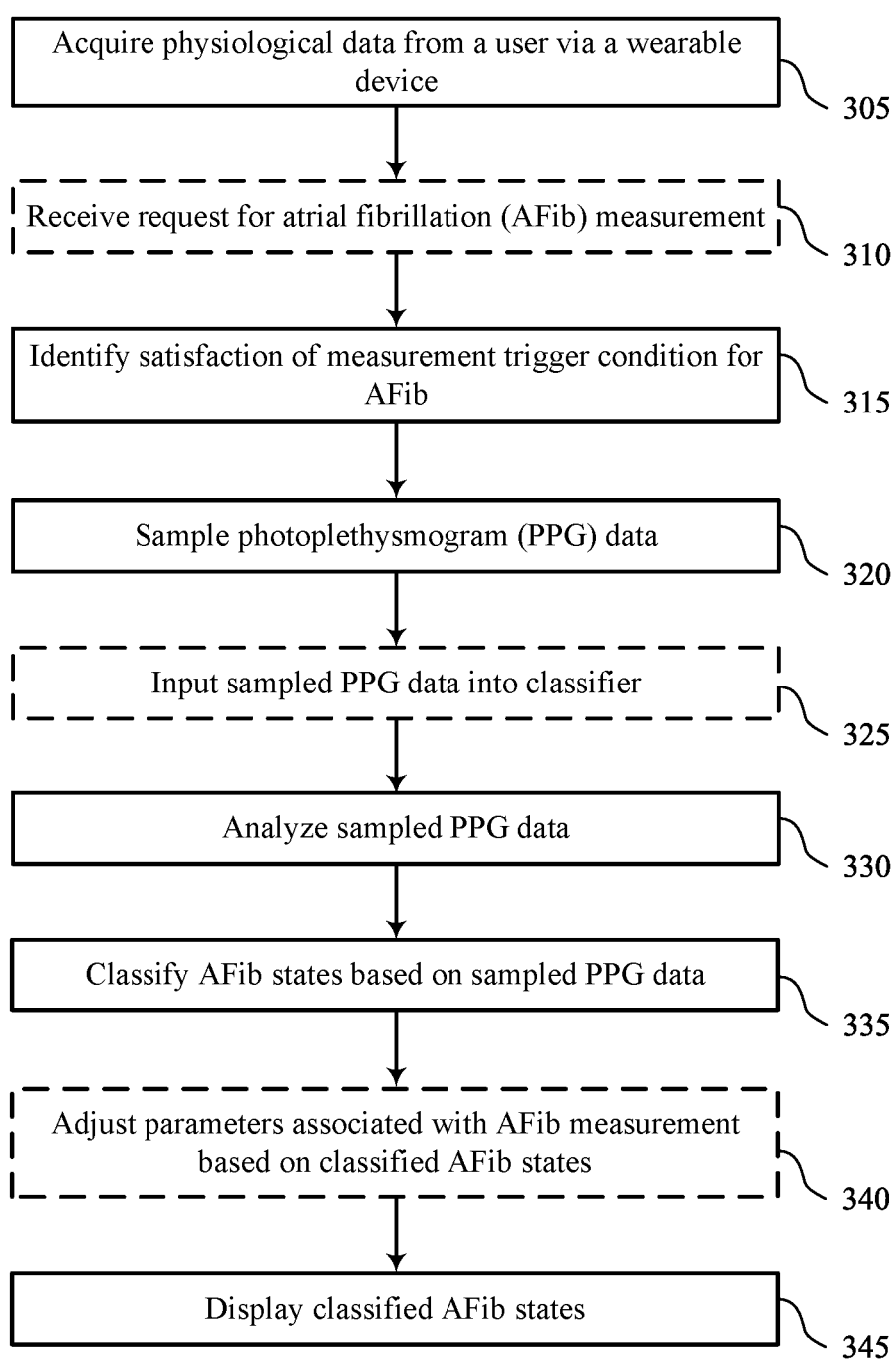

FIG. 3 illustrates an example of a process flow 300 that supports techniques for detecting AFib in accordance with aspects of the present disclosure. In some examples, the process flow 300 may implement, or be implemented by, aspects of system 100, system 200, or both. In particular, the process flow 300 illustrates steps and operations for detecting AFib using a wearable device 104, in accordance with aspects of the present disclosure. For example, the various steps/functions of the process flow 300 may be performed by any of the various components of system 200, including the wearable device 104, the user device 106, the servers 110, or any combination thereof.

At 305, the system 200 may acquire physiological data from a user via a wearable device 104. For example, the system 200 may acquire physiological data from a user via a wearable ring device 104. In such cases, the wearable ring device 104 may acquire physiological data from a user based on arterial blood flow (e.g., arterial blood flow in the user's finger). Physiological data acquired from the user may include temperature data, motion data (e.g., accelerometer data), heart rate data, HRV data, respiratory rate data, blood oxygen saturation data, and the like.

At 310, the system 200 may receive a request for AFib measurement from a user. For example, the system 200 may receive a user input including a request for AFib measurement via a user device 106. In other words, a user may be able to manually initiate an AFib spot-check by inputting a request via the user device 106.

At 315, the system 200 may identify a satisfaction of one or more measurement trigger conditions for AFib measurement. In some aspects, the system 200 may evaluate a satisfaction (or lack thereof) of measurement trigger conditions based on acquiring the physiological data at 305, receiving the request at 310, or both. Measurement trigger conditions may include any trigger conditions of AFib measurement criteria that are used to trigger AFib measurement during periods of time that are likely to achieve high quality AFib measurements. For example, the system 200 may evaluate whether it is a good time to perform AFib measurements (e.g., whether measurement trigger conditions are satisfied) upon receiving the request at 310.

In some aspects, the system 200 may evaluate whether measurement trigger conditions for AFib measurement has been satisfied based on acquired temperature data satisfying a temperature threshold, acquired motion data satisfying a motion threshold, or both. For example, in some cases, the system 200 may identify a satisfaction of one or more measurement trigger conditions in cases where the user exhibits high temperature (e.g., $T \geq T_{Thresh}$) and low movement/motion (e.g., (e.g., $M \leq M_{Thresh}$) In some implementations, the system 200 may evaluate a satisfaction (or lack thereof) of measurement trigger conditions for AFib measurement in accordance with a regular periodicity, an irregular periodicity, or both. In additional or alternative implementations, the system 200 may evaluate a satisfaction (or lack thereof) of measurement trigger conditions based on (e.g., in response to) receiving the request at 310.

At 320, the system 200 may sample PPG data for the user via the wearable device. In other words, the wearable device may sample (e.g., collect) PPG data from the user using one or more sensors (e.g., LEDs, photodiodes) of the wearable device. In some aspects, the wearable device may sample PPG data based on acquiring the physiological data at 305, receiving the request for AFib measurement at 310, identifying the satisfaction of one or more trigger conditions at 315, or any combination thereof. In some implementations, sampled PPG data may be transmitted from the wearable device 104 to the user device 104, the servers 110, or both.

At 325, the system 200 may input sampled PPG data that may be input into a classifier. For example, in some implementations, the servers 110 of the system 200 may receive sampled PPG data, and may input sampled PPG data into a classifier, such as a machine learning classifier, a random forest classifier, a neural network, and the like. In some aspects, the system 200 may be configured to extract features from the sampled PPG data, and input the extracted features into a classifier. For example, the system 200 (e.g., ring 104, user device 106, servers 110) may be configured to extract features of the sampled PPG data and/or IBI series including, but not limited to, root mean square of successive difference (RMSSD), normalized RMSSD (nRMSSD), sample entropy, zero-ratio, trajectory variability, and the like. In general, any features associated with acquired physiological data and/or the sampled PPG data may be extracted and input into the classifier.

At 330, the system 200 may analyze the sampled PPG data. The system 200 may analyze the sampled PPG data using any techniques known in the art. For example, in some implementations, the system 200 may analyze the sampled PPG data based on inputting the PPG data into a classifier at 325. In other words, the classifier may be configured to analyze the sampled PPG data. In additional or alternative implementations, the system 200 may analyze the sampled PPG data using techniques and resources other than a classifier. For example, in some cases, the system 200 may be configured to extract features from the sampled PPG data and analyze the extracted features using techniques and resources other than a classifier.

Details regarding the analysis of sampled PPG data at 330 will be discussed in further detail herein with respect to FIG. 4.

At 335, the system 200 may classify one or more AFib states. The one or more AFib states may include, but are not limited to, a positive AFib state, a negative AFib state, a potential AFib state, an inconclusive AFib state, or any combination thereof. In this regard, the system 200 may classify the one or more AFib states based on sampled PPG data in order to determine one or more AFib states associated with the user that may then be used to evaluate a relative AFib risk level for the user.

In some aspects, the system 200 may classify the one or more AFib states based on acquiring the physiological data at 305, receiving the request at 310, identifying the satisfaction of one or more measurement trigger conditions at 315, sampling the PPG data at 320, inputting the sampled PPG data at 325, analyzing the sampled PPG data at 330, or any combination thereof.

At 340, the system 200 may selectively adjust one or more parameters associated with AFib measurement based on the one or more classified AFib states determined at 335. Parameters for AFib measurement that may be selectively modified may include, but are not limited to, a measurement periodicity (e.g., periodicity when AFib is measured), a power level associated with one or more sensors used to sample PPG data, and the like.

For example, in cases where the system 200 determines a positive AFib state or a potential AFib state (or some other AFib state), the system 200 may increase a periodicity when AFib is measured or evaluated. By way of another example, in cases where the system 200 determines an inconclusive AFib state, the system 200 may increase a power level supplied to LEDs that are used to sample PPG data for AFib measurement. Increasing a power level provided to PPG sensors (e.g., LED) may enable higher quality PPG data that may be used to more accurately and reliably detect a presence (or lack thereof) of AFib characteristics.

At 345, the system 200 may cause a GUI of a user device 106 to display an indication of the one or more classified AFib states. For example, the user device 106 illustrated in FIG. 2 may display an indication of classified AFib states via the GUI 275. In some implementations, the system 200 may also display messages or other guidance associated with the classified AFib states. AFib-related messaging and guidance may include any guidance, including a predicted upcoming AFib episode, an expected severity/duration of an AFib episode, an instruction for user action that may prevent or reduce a severity of an AFib episode, an identified trigger for an AFib episode, and the like.

Indications of classified AFib states and other AFib-related guidance that may be provided to a user will be described in further detail herein with respect to FIG. 8.

Figure 4:
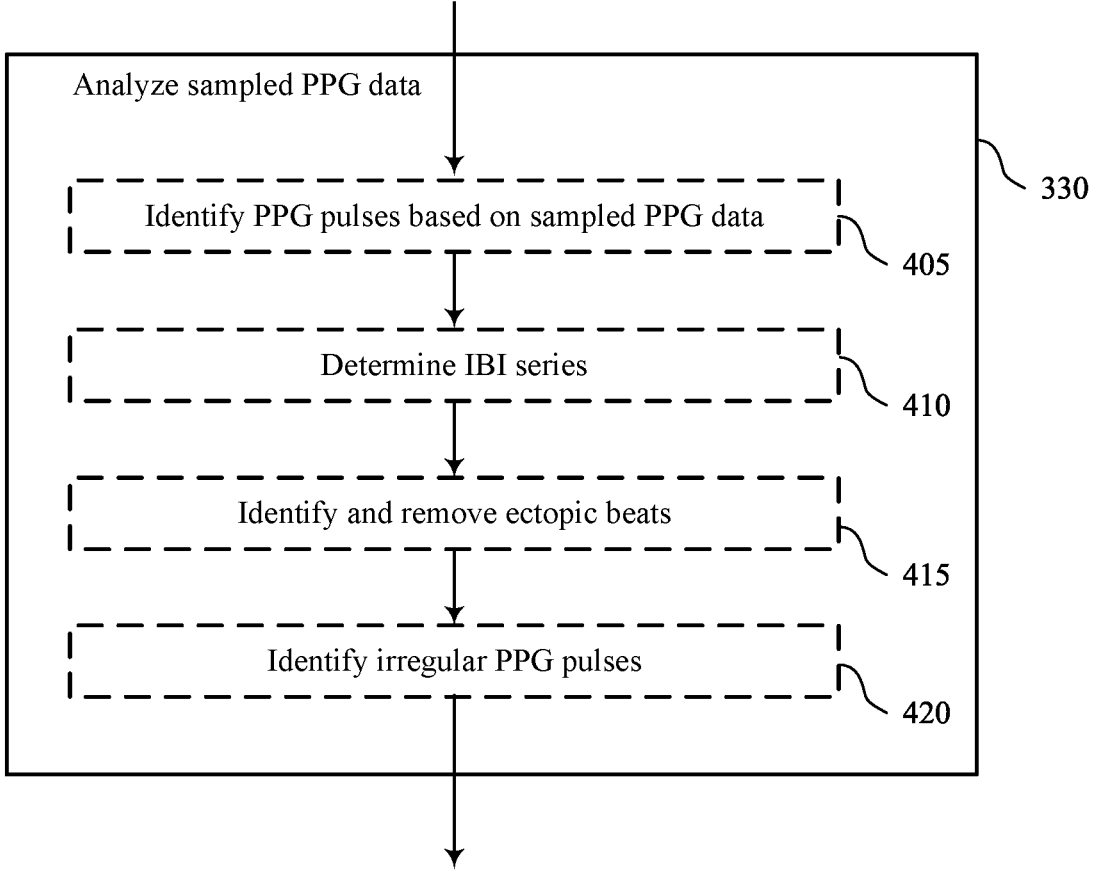

FIG. 4 illustrates an example of a process flow 400 that supports techniques for detecting AFib in accordance with aspects of the present disclosure. In some examples, the process flow 400 may implement, or be implemented by, aspects of system 100, system 200, the process flow 300, or any combination thereof. For example, the various steps/functions of the process flow 400 may be performed by any of the various components of system 200, including the wearable device 104, the user device 106, the servers 110, or any combination thereof.

The process flow 400 illustrates sub-steps and sub-operations of 330 illustrated in the process flow 300 for detecting AFib using a wearable device 104, in accordance with aspects of the present disclosure. In particular, the process flow 400 illustrates sub-steps and sub-operations for analyzing sampled PPG data, as shown in 330 of the process flow 300. In some aspects, the steps/functions of the process flow 400 may be performed by a classifier, such as a machine learning classifier, a random forest classifier, a neural network, and the like. Additionally, or alternatively, the steps/functions of the process flow 400 may be implemented by techniques and/or resources other than classifiers, such as via processors of the user device 106 and/or servers 110 illustrated in FIGS. 1-2.

At 405, the system 200 may identify a set of PPG pulses for the user based on the PPG data that was sampled at 320 of the process flow 300. In some cases, the system 200 may identify the PPG pulses based on inputting the sampled PPG data into the classifier at 325 (e.g., the classifier may be configured to identify PPG pulses).

At 410, the system 200 may determine an IBI series for the user based on the set of PPG pulses that were identified at 410. In some, the system 200 may identify the IBI series based on inputting the sampled PPG data into the classifier at 325 (e.g., the classifier may be configured to identify the IBI series).

It has been found that up to 75% of the general population experience premature atrial contractions (PACs) and/or premature ventricle contractions (PVCs). These premature contractions (e.g., extrasystoles) may result from a wide range of factors, including physical and mental stress, low levels of potassium and magnesium, heavy alcohol, nicotine, or coffee consumption, underlying cardiac disease, and the like. In some cases, premature contractions may disturb the measurement of physiological data, such as PPG data, heart rate data, and HRV data. In general, these premature contractions may be referred to as "ectopic beats." Ectopic beats may also be characterized by an extra or skipped heartbeat, or a heartbeat that exhibits abnormal timing.

Although abnormal, ectopic beats are generally not indicative of AFib. That is, the irregularity of ectopic beats is not indicative of the "irregularly irregular" heartbeat that is indicative of AFib. As such, it has been found that the identification (and removal) of ectopic beats (e.g., PACs, PVCs) may lead to improved physiological data measurement and improved AFib detection. In other words, AFib detection may be improved by removing PPG pulses and heart beats from identified PPG pulses/IBI series that are attributable to ectopic beats. Accordingly, in some implementations, the process flow 400 may proceed to 415 for identification and removal of ectopic beats.

At 415, the system 200 may identify and remove one or more ectopic beats from the set of PPG pulses identified at 405 and/or the IBI series identified at 410. That is, the system 200 may identify PPG pulses that are attributable to ectopic beats, and may remove the identified PPG pulses from the set of identified PPG pulses. Stated more generally, the system 200 may be configured to identify one or more irregular PPG pulses/heartbeats that are attributable to some other physiological condition other than AFib, and may remove the identified PPG pulses/heartbeats from the set of PPG pulses/IBI series. Subsequently, the edited PPG pulses/IBI series (e.g., PPG pulses/IBI series with ectopic beats removed) may be analyzed for AFib.

The identification and removal of ectopic beats for improved AFib detection may be further shown and described with reference to FIG. 5.

Figure 5:
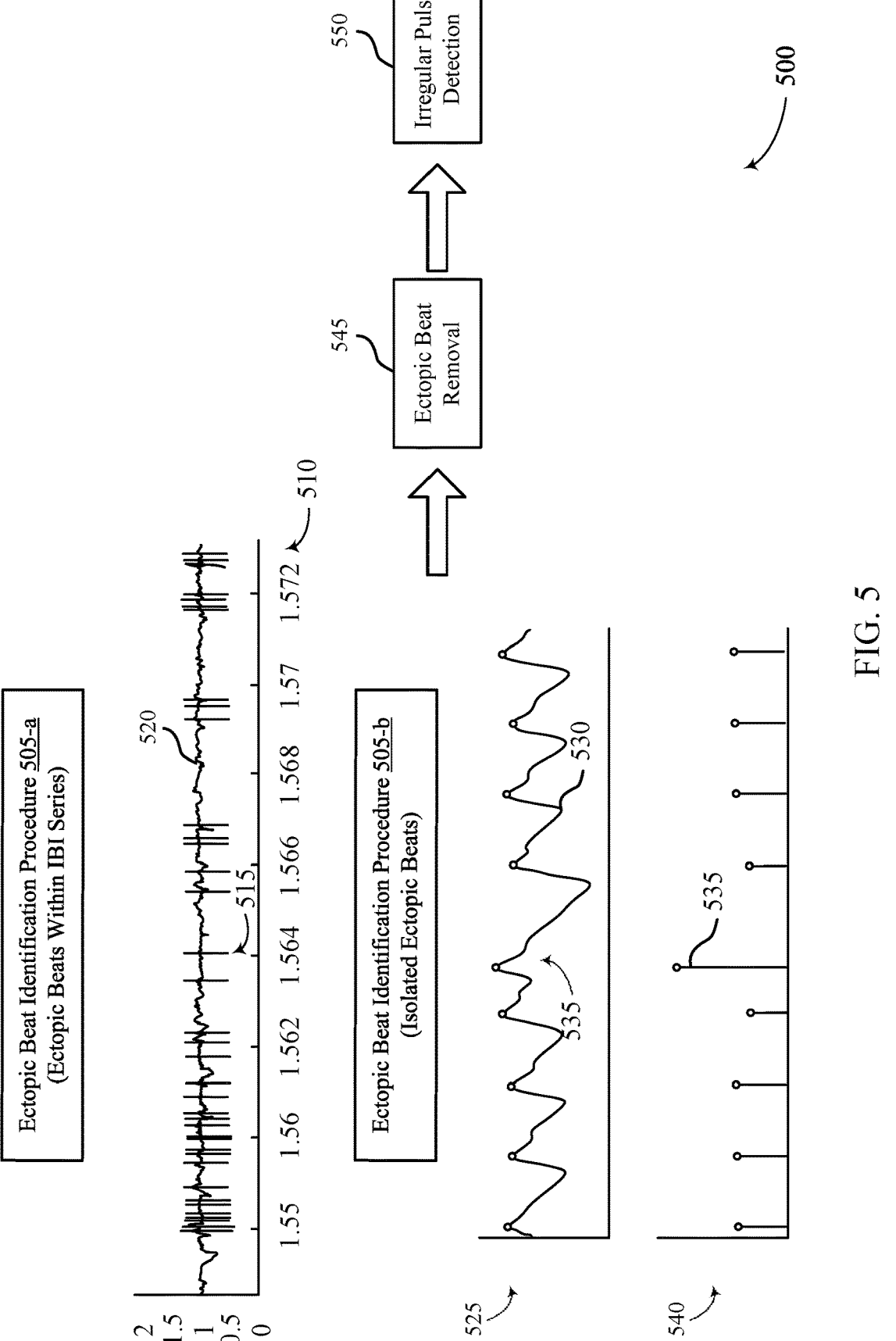

FIG. 5 illustrates an example of a process flow 500 that supports techniques for detecting AFib in accordance with aspects of the present disclosure. In some examples, the process flow 500 may implement, or be implemented by, aspects of system 100, system 200, the process flow 300, the process flow 400, or any combination thereof. In particular, the process flow 500 illustrates additional or alternative steps and operations of the process flow 300 for detecting AFib using a wearable device 104, in accordance with aspects of the present disclosure.

Since ectopic beats disrupt the normal sinus rhythm, techniques described herein may be used to reduce an impact on the parameters that are calculated from the IBI series by identifying and removing ectopic beats from the IBI series. This can be done by identifying ectopic patterns and subtracting them from the IBI series prior to the analysis. As will be described in further detail herein, the AFib detection algorithms described herein may identify and remove ectopic beats in two separate steps (1) in the analysis of the IBI series (e.g., prior to IBI feature extraction), and (2) prior to analysis of beat morphology. For example, as shown in FIG. 5, the process flow 500 may include a first ectopic beat identification procedure 505-*a* that identifies ectopic beats within the IBI series, and a second ectopic beat identification procedure 505-*b* that identifies isolated ectopic beats prior to beat morphology analysis.

Referring to the first ectopic beat identification procedure 505-*a*, in some aspects, the system 200 may analyze the IBI series to determine heart rate differences ΔHR between consecutive heart beats of the IBI series. In some aspects, the system 200 may utilize one or more algorithms or plots (e.g., scatter plot) in order to identify heart beats and heart beat segments that are attributable to normal sinus rhythm, and heart beats and heart beat segments that are attributable to AFib. For example, by plotting the IBI series for a user within a scatter plot, trajectories for heart beats associated with normal sinus rhythm may be predominantly positioned within a central region of the scatter plot, whereas heart beats associated with AFib may exhibit irregular trajectories (e.g., trajectories without a clear pattern) toward the periphery of the scatter plot. In other words, ectopic beaths may exhibit their own patterns within a scatter plot, whereas AFib may exhibit chaotic and random patterns within the plot. As such, the use of scatter plots may enable ectopic beats to be extracted from the heart rate trajectories within the scatter plot for more reliable AFib detection.

In some cases, the complexity of the IBI series (e.g., edited IBI series curve 520) during normal sinus rhythm may be expected to be low, whereas AFib may produce an IBI series with high complexity due to the high irregularity of AFib. The zero-ratio parameter may be defined as a percentage of all scatter plot samples that are within a central region of the plot (e.g., range from 0 to 100), and a trajectory variability parameter may be calculated as a variance of consecutive sample locations within each segment, where low values indicate low variability and high values indicate high variability. It has been found that the detection and subtraction of ectopic patterns prior to the measurement of the IBI-based parameters via the first ectopic beat identification procedure 505-*a* may significantly reduce false-positive AFib determinations, and improve AFib detection.

Upon identifying patterns of ectopic beats (e.g., ectopic beats within the scatter plot), identified ectopic beats may be removed from the IBI series. For example, referring to graph 510, the identified ectopic beats may be removed from an unedited IBI series curve 515 via the ectopic beat removal 545 to generate the edited IBI series curve 520. While patterns associated with ectopic beats may also be present in an AFib IBI series, it has been found that AFib may still be detected within the edited IBI series curve 520, such that the removal of ectopic beats from the IBI series may enable improved AFib detection. In other words, filtering/editing the IBI series in accordance with the first ectopic beat identification procedure 505-*a* has been found to improve pattern recognition for improved AFib detection.

After the subtraction of ectopic patterns in accordance with the first ectopic beat identification procedure 505-*a*, the system 200 may perform feature analysis for the IBI series. In other words, the system 200 may identify features associated with the edited IBI series curve 520 after the removal of ectopic beats. When extracting features from the IBI series, the regularity and complexity of the IBI series may be assessed over some time interval (e.g., 60-second time intervals). Features of the IBI series that may be determined may include, but are not limited to, RMSSD, nRMSSD, sample entropy, zero-ratio, trajectory variability, and the like.

For example, the system 200 may identify at least one ectopic beat from the set of PPG pulses that were identified at 405 of the process flow 400, and may remove the at least one ectopic beat from the set of PPG pulses to generate a reduced set of PPG pulses (e.g., remove ectopic beats from unedited IBI series curve 515 to generate edited IBI series curve 520). The reduced set of PPG pulses (e.g., edited IBI series curve 520) may then be evaluated to detect AFib, as will be described in further detail herein.

Ectopic beats may be identified within (and removed from) the IBI series based on one or more characteristics of the ectopic beats. In particular, identified PPG pulses may be compared to a baseline PPG pulse in order to detect ectopic beats. Characteristics of PPG pulses that may be used to identify PPG pulses associated with ectopic beats may include, but are not limited to, a timing of PPG pulses (e.g., relative timing of PPG pulses relative to adjacent PPG pulses), an amplitude of the PPG pulses, a time interval/duration of the PPG pulses, or any combination thereof.

Reference will now be made to the second ectopic beat identification procedure 505-*b* illustrated in FIG. 5. As noted previously herein, the system 200 may be configured to implement a separate procedure for identifying and removing ectopic beats from the IBI series/PPG pulses for improved AFib detection. As such, the second ectopic beat identification procedure 505-*b* may be implemented independently from the first ectopic beat identification procedure 505-*a*.

In some aspects, the second ectopic beat identification procedure 505-*b* may be performed prior to the analysis of beat morphology to identify isolated ectopic beats (e.g., ectopic beats that are surrounded by normal heart beats). In some aspects, the second ectopic beat identification procedure 505-*b* may identify isolated ectopic beats based on both the IBI series (e.g., unedited IBI series curve 515, edited IBI series curve 520), as well as pulse amplitudes associated with the respective PPG pulses/heart beats within the IBI series. Both the IBI series and pulse amplitude/morphology will be affected by the ectopic beats. As such, in accordance with the second ectopic beat identification procedure 505-*b*, the system 200 may be configured to analyze the ratio between consecutive IBI intervals (e.g., consecutive beats/PPG pulses), as well as the amplitude ratios of consecutive beats, in order to identify ectopic beats.

For example, amplitude ratios of descending and ascending limbs of each heart beat/PPG pulse may be used to identify ectopic beats. For instance, referring to graph 525, ascending limbs of PPG pulses may be defined by a signal increase between troughs and subsequent peaks in the PPG curve 530, where descending limbs of PPG pulses may be defined by a signal decrease between peaks and subsequent troughs in the PPG curve 530. Thus, an amplitude ratio of descending and ascending limbs of each PPG pulse may be defined as a ratio of signal decrease following each PPG pulse to the signal increase leading up to each PPG pulse (e.g., descending/ascending). Ratios of descending and ascending limbs of each PPG pulse of the PPG curve 530 are illustrated in graph 540. For example, the ratio of descending and ascending limbs of the PPG pulse 535 within the PPG curve 530, as illustrated in graph 540, may be used to identify that the PPG pulse 535 is likely attributable to an ectopic beat. Such ratios may be calculated to identify any type of ectopic beats, such as PVCs.

Subsequently, as illustrated in FIG. 5, identified ectopic beats may be removed at 545. In other words, PPG pulses associated with ectopic beats may be removed from the IBI series/set of identified PPG pulses. Ectopic beats may be identified/removed in accordance with the first ectopic beat identification procedure 505-*a*, the second ectopic beat identification procedure 505-*b*, or both. For example, the removal of identified ectopic beats at 545 may be used to transform the unedited IBI series curve 515 into the edited IBI series curve 520. In general, the removal of ectopic beats may be used to generate an edited IBI series (e.g., edited IBI series curve 520) and a revised/edited set of PPG pulses that may be analyzed for AFib. In other words, after removing ectopic beats at 545, the edited IBI series curve 520 (e.g., edited/revised IBI series or edited set of PPG pulses) may be analyzed at 550 for irregular pulses that may be attributable to AFib.

The analysis of the edited/revised IBI series (e.g., edited/revised set of PPG pulses) performed at 550 in FIG. 5 may be further shown and described with reference to 420 illustrated in FIG. 4. As such, reference will again be made to FIG. 4.

At 420, the system 200 may identify one or more irregular PPG pulses that may be attributable to AFib. In particular, the system 200 may analyze an edited/revised set of PPG pulses (e.g., edited IBI series curve 520) for irregular pulses based on identifying and removing ectopic beats at 515. For example, as described in FIG. 5, the system 200 may identify and remove ectopic beats in accordance with ectopic beat identification procedures 505, and may perform irregular pulse detection at 550. In this regard, the irregular pulse detection at 550 illustrated in FIG. 5 may include an example of the irregular PPG pulse detection at 420 illustrated in FIG. 4, and vice versa.

In some cases, irregular PPG pulses that may be attributable to AFib may be identified by comparing PPG pulses to a baseline PPG pulse. For example, PPG pulses may be compared to a baseline PPG pulse to determine a metric with that the PPG pulses must be "stretched" or "shrunk" to match the time interval/duration of the baseline PPG pulse. This "dynamic time-warping" of PPG pulses may be used to assess the overall variability between pulses. In this example, the mean pulse may be calculated from the entire IBI series, where each PPG pulse is stretched (or compressed) to match the mean pulse. The distance with that each PPG pulse was stretched/compressed to match the mean pulse (e.g., baseline PPG pulse) may be separately calculated for each respective PPG pulse. PPG pulses associated with normal sinus rhythm may generally require little stretching/compression to match the baseline PPG pulse, whereas PPG pulses associated with AFib may require more stretching/compression to match the baseline PPG pulse.

The identification of irregular PPG pulses that may be attributable to AFib, that is performed at 420, may be used to perform the classification of AFib states at 335 of the process flow 300. That is, identified irregular PPG pulses may be used to classify one or more AFib states for the user in order to evaluate a relative AFib risk for the user.

In some cases, the use of sampled PPG data to classify AFib states may be performed as a "preliminary" AFib assessment. Moreover, in some cases, classified AFib states that are determined and presented to the user at 420 may be used to perform additional measurements and determinations that may be used to more accurately and reliably detect AFib. In other words, upon determining initial AFib states for the user, the system 200 may be configured to perform additional measurements (e.g., ECG measurements) that may be used to refine, confirm/verify, and/or dismiss classified AFib states. This may be further shown and described with reference to FIG. 6.

FIG. 6 illustrates an example of a process flow 600 that supports techniques for detecting AFib in accordance with aspects of the present disclosure. In some examples, the process flow 600 may implement, or be implemented by, aspects of system 100, system 200, the process flow 300, the process flow 400, the process flow 500, or any combination thereof. For example, the various steps/functions of the process flow 600 may be performed by any of the various components of system 200, including the wearable device 104, the user device 106, the servers 110, or any combination thereof.

The process flow 600 illustrates additional and/or alternative steps/functions that may be performed in conjunction with the process flow 300 illustrated in FIG. 3, the process flow 400 illustrated in FIG. 4, or both. For example, as shown in FIG. 6, the steps/functions of the process flow 600 may be performed subsequent to displaying classified AFib states to the user at 345 of the process flow 300.

At 605, the system 200 may display a prompt for performing an ECG measurement. In some cases, the system 200 may display the prompt for the ECG measurement based on (e.g., in response to) classifying and/or displaying the AFib states for the user. For example, the system 200 may display a prompt for an ECG measurement after classifying a positive, potential, and/or inconclusive AFib state at 335 of the process flow 300, displaying the classified AFib states at 345, or both.

At 610, the system 200 may receive a user input for performing an ECG measurement. In some aspects, the system 200 may receive the user input at 610 based on (e.g., in response to) displaying the prompt at 605. For example, in some cases, a user may confirm or initiate an ECG measurement for more accurate AFib detection in response to the prompt displayed at 605.

At 615, the system 200 may display instructions for performing ECG measurements. The system 200 may display the instructions at 615 based on displaying the prompt at 605, receiving the user input at 610, or both. For example, in the context of a wearable ring device 104, the system 200 may display a message instructing the user to relax, and may provide instructions on how the user is to position the wearable ring device 104 in order to perform accurate ECG measurements. For example, as will be described in further detail herein with respect to FIG. 8 below, the system 200 may instruct the user to press the wearable ring device 104 against the user's chest or another part of their body (e.g., the user's other hand) in order to close the circuit to record ECG measurements.

The various steps/functions shown and described at 605-615 of the process flow 600 may be further shown and described with reference to FIG. 7.

Figure 7:
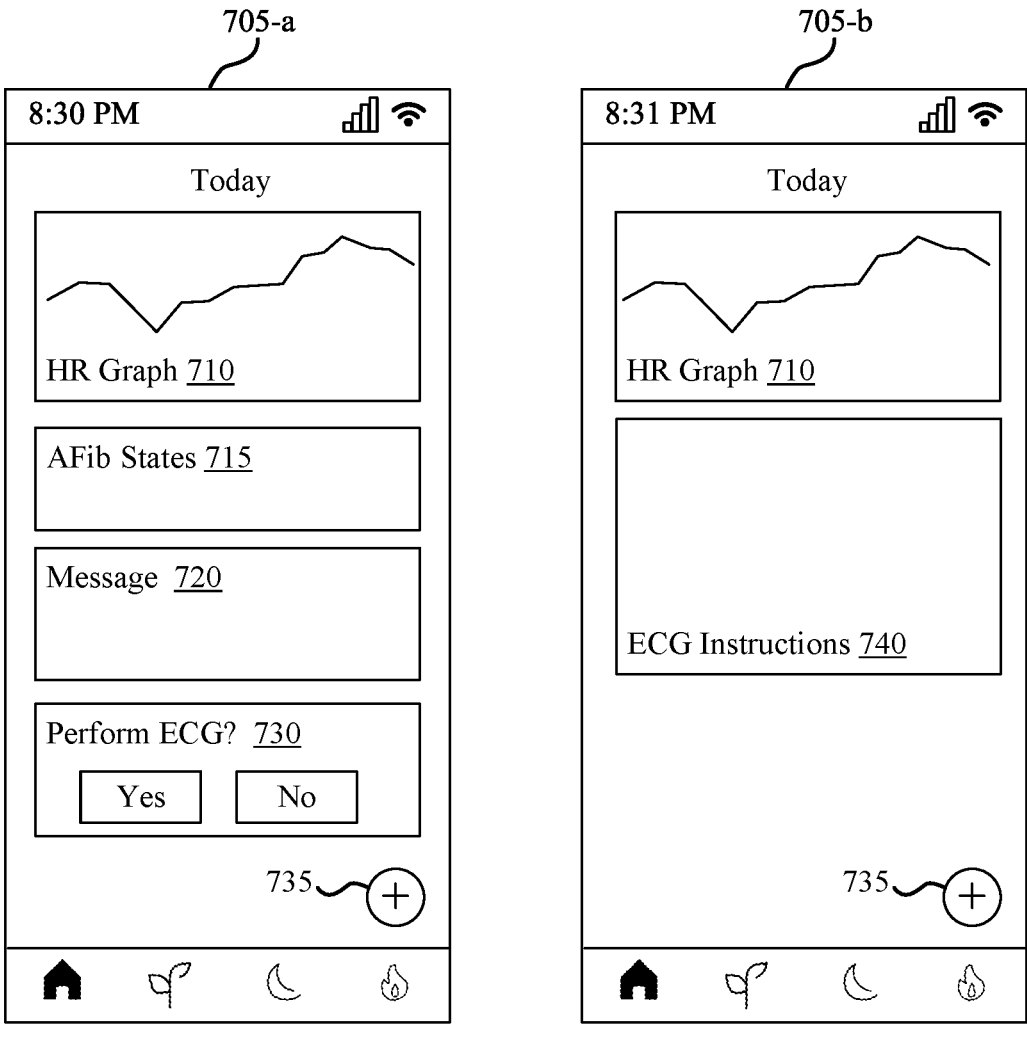
FIG. 7 illustrates an example of a graphical user interface (GUI) that supports techniques for detecting AFib in accordance with aspects of the present disclosure.

FIG. 7 illustrates an example of a GUI 700 that supports techniques for detecting AFib in accordance with aspects of the present disclosure. The GUI 700 may implement, or be implemented by, aspects of the system 100, system 200, the process flows 300-600, or any combination thereof. For example, the GUI 700 illustrated in FIG. 7 may include an example of the GUI 275 included within the user device 106 illustrated in FIG. 7.

The GUI 700 illustrates a series of application pages 705 that may be displayed to the user via the GUI 700 (e.g., GUI 275 illustrated in FIG. 2). For example, the server 110 of system 200 may cause the GUI 700 of the user device 106 (e.g., mobile device) to display a heart rate graph 710 via application page 705-a. As shown in application page 705-a, the GUI 700 may display one or more classified AFib states for the user (e.g., AFib states classified at step 345 of the process flows 300 and 600). Classified AFib states may include, but are not limited to, a positive AFib state, a negative AFib state, a potential AFib state, an inconclusive AFib state, and the like. Additional or alternative AFib states may also be used. In general, classified AFib states may indicate a relative AFib risk level for each respective user.

In some aspects, the application page 705-a may display one or messages 720 or other guidance associated with the classified AFib states 715. In other words, the application page 705-a may provide tailored guidance to a user that is aimed to reduce the user's risk for AFib episodes. In this regard, AFib states 715 may be displayed/presented to the user along with messaging (e.g., message 720) that provides more information associated with the respective AFib state.

For example, upon detecting a potential/possible AFib state, the message 720 may read: "Possible AFib detected: You may wish to confirm this with a clinician or run a 12-lead ECG to check for other possible abnormalities." By way of another example, upon detecting a negative AFib state, the message 720 may read: "Normal: Your heart rate and rhythm are normal with no or very few abnormal beats." Comparatively, upon detecting an inconclusive AFib state, the message 720 read "Unclassified: The algorithm was not able to classify your heart beat as AFib or normal," or "Unreadable: The recording was not readable due to interference. Try to relax and hold still for a better measurement; rest your arms or move to a quiet location. Ensure your ring is placed correctly and the sensors are clean."

The message 720 may provide additional guidance associated with classified AFib states 715, such a predicted upcoming AFib episode, an expected severity/duration of an AFib episode, an instruction for user action that may prevent or reduce a severity of an AFib episode, an identified trigger for an AFib episode, and the like. In some cases, the application pages 705 may include a user input component 735 that enables users to "tag" events or subjective feelings to help improve the identification, prediction, and prevention of AFib triggers for each respective user.

For example, users may select the user input component 735 to tag or input the use of potential "triggers" (e.g., alcohol, caffeine, poor sleep, anxiety episodes) via a user device. In such cases, AFib detection algorithms described herein may identify potential triggers for AFib episodes for each respective user, and may algorithmically determine the likelihood that a trigger is followed by an AFib episode, as well as predict a severity or duration of an AFib episode. In this regard, AFib detection algorithms described herein may be configured to associate detected AFib occurrences/episodes with user behavior and lifestyle choices, as determined based acquired physiological data and "tags" that are input by a user. In this regard, the system may be configured to learn (e.g., via algorithms, classifiers, or other machine learning techniques) that triggers/behavioral choices are likely to be followed by an AFib episode, and may therefore predict AFib occurrences prior to onset. Furthermore, by identifying triggers that are likely to lead to AFib occurrences, techniques described herein may provide guidance that is tailored to the user in order to reduce a frequency, likelihood, or severity of AFib episodes (e.g., guidance that suggests the user reduce a frequency of AFib triggers, guidance that suggests that the user exercise or perform other actions that have been found to reduce AFib occurrences, etc.).

In some implementations, a user may be able to trigger an AFib "spot check" by selecting the user input component 735. For example, the user may launch the PPG-based spot-check simply by tapping the user input component 735 in the lower right-hand corner of the application page 705-*a*, This may trigger the PPG sampling for some time interval (e.g., 30-60 seconds) during that the user's heart rhythm is analyzed.

Moreover, as shown in FIG. 7, the application page 705-*a* may display a prompt 730 for performing an ECG measurement. In some cases, the system 200 may display the prompt 730 for the ECG measurement based on (e.g., in response to) classifying and/or displaying the AFib states 715 for the user. In some aspects, the prompt 730 may include user input options that enable the user to initiate ECG measurements, dismiss the prompt 730, and the like. For example, the user may be able to select "Yes" within the prompt 730 in order to initiate ECG measurement that may be used to improve AFib detection. In this regard, the system 200 may receive a user input that confirms/initiates ECG measurement.

Upon receiving the user input to perform the ECG measurement, the GUI 700 may display application page 705-*b* that includes ECG instructions 740. In some aspects, the ECG instructions 740 may include any messaging or guidance that helps the user perform accurate ECG measurements. For example, the ECG instructions 740 may instruct the user to lie down and to relax. Additionally, or alternatively, the ECG instructions may provide guidance for positioning the wearable device 104 to perform ECG measurements. For example, in the context of a wearable ring device 104, the ECG instructions 740 may instruct the user to place their hand against their chest such that the palm-side surface of the wearable ring device 104 contacts the skin on the user's chest proximate to their heart in order to close the circuit for ECG measurement.

In some cases, the ECG instructions may indicate how long the user is to maintain a certain position for ECG measurement. Moreover, in some cases, the ECG instructions 740 may be supplemented with other indications, such as audio or haptic feedback (e.g., beeps, vibrations) of the user device in order to facilitate ECG measurement. For example, the user device may play a tone or beeps that indicate a beginning and end of the ECG measurement.

Reference will again be made to the process flow 600 illustrated in FIG. 6.

At 620, system 200 may collect ECG data for the user via the wearable device 104 (e.g., wearable ring device 104). In other words, the system 200 may perform ECG measurements via the wearable device 104. In some aspects, the system 200 may collect ECG data based on displaying the prompt for ECG measurement at 605, receiving the user input for ECG measurement at 610, displaying the instructions for ECG measurement at 615, or any combination thereof.

In some aspects, the wearable device 104 may collect the ECG data (e.g., perform the ECG measurement) by measuring a voltage differential across conductive components of the wearable device. For example, in the context of a wearable ring device 104, the wearable ring device 104 may collect ECG data by measuring a voltage differential between an inner surface of the wearable ring device 104 and an outer surface of the wearable ring device 104. In such cases, the wearable ring device 104 may have dedicated electrodes on the inner and outer surfaces that are configured to conduct electrical currents in order to measure the voltage differential. Additionally, or alternatively, the wearable ring device 104 may include a conductive frame or other conductive component that serves as an electrode on the inner surface, the outer surface, or both. The use of a wearable ring device 104 to perform ECG measurements will be described in further detail herein with respect to FIG. 8.

At 625, the system 200 may classify or identify one or more additional AFib states based on the collected ECG data. The one or more additional AFib states may be the same or different as the AFib states that were classified at 335 of the process flow 300. In this regard, any description associated with step 335 of the process flow 300 may be regarded as applying to 625 in the process flow 600, to the extent applicable, and unless noted otherwise herein. For example, in some cases, the system 200 may input collected ECG data into a classifier (e.g., machine learning classifier, random forest classifier, neural network), where the classifier is configured to classify one or more AFib states associated with the user based on the collected ECG data, the sampled PPG data, or both.

At 630, the system 200 may cause a GUI of a user device to display an indication of the one or more AFib states that were classified at 625. For example, the user device 106 illustrated in FIG. 2 may display an indication of classified AFib states via the GUI 275. Any description associated with step 345 of the process flow 300 may be regarded as applying to step 630 in the process flow 600, to the extent applicable, and unless noted otherwise herein. For example, as noted previously herein, in some implementations, the system 200 may also display messages or other guidance associated with the classified AFib states. AFib-related messaging and guidance may include any guidance, including a predicted upcoming AFib episode, an expected severity/duration of an AFib episode, an instruction for user action that may prevent or reduce a severity of an AFib episode, an identified trigger for an AFib episode, and the like.

Figure 8:
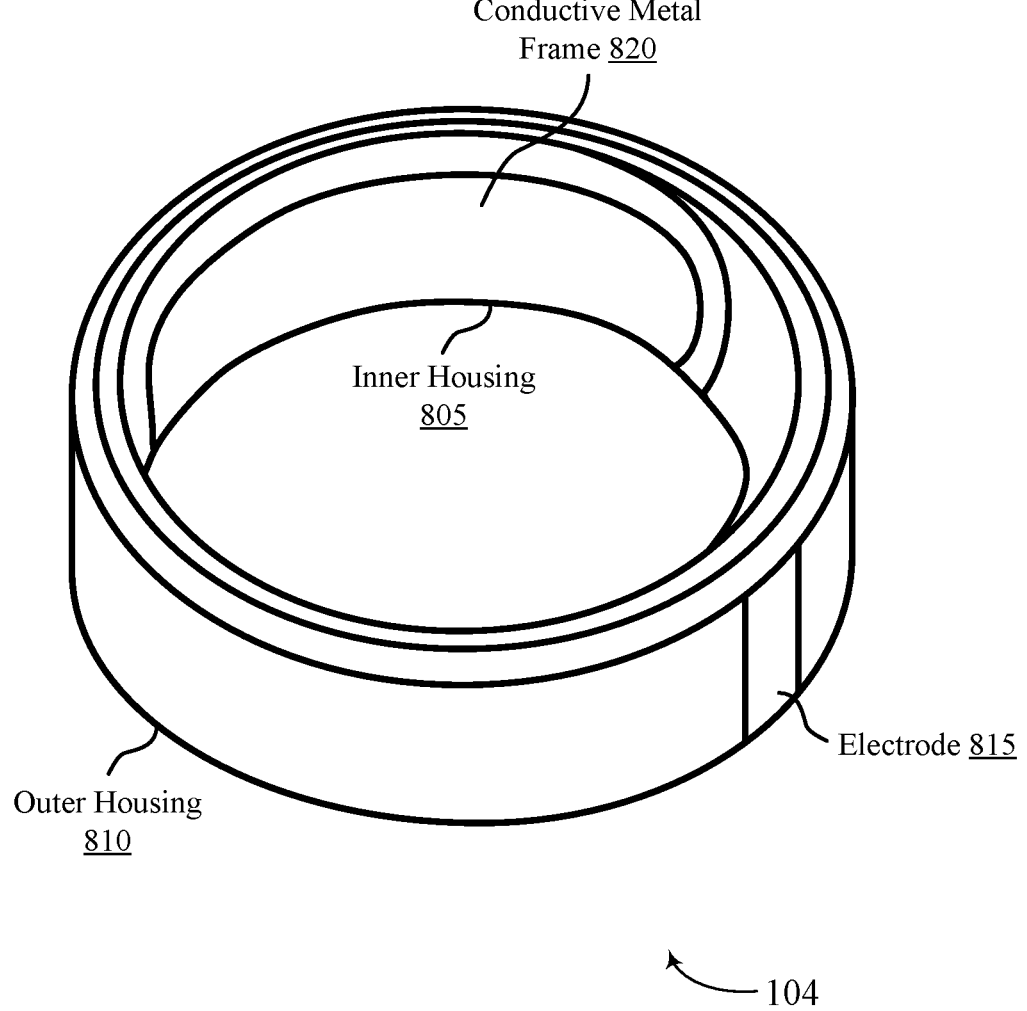
FIG. 8 illustrates an example of a perspective diagram of a wearable ring device that supports techniques for detecting AFib in accordance with aspects of the present disclosure.

FIG. 8 illustrates an example of a perspective diagram 800 of a wearable ring device 104 that supports techniques for detecting AFib in accordance with aspects of the present disclosure. In particular, the wearable ring device 104 illustrated in FIG. 7 may include an example of a wearable ring device 104 as shown and described with reference to FIGS. 1-6.

In some aspects, the wearable ring device 104 may include an inner housing 805 and an outer housing 810, where the inner housing 805 and the outer housing 810 are configured to contain/house the various components and sensors of the wearable ring device 104, as described in FIG. 2. As noted previously herein, in some aspects, the wearable ring device 104 may be configured to perform ECG measurements by measuring a voltage differential across portions of the wearable ring device 104. For example, in some implementations, the wearable ring device 104 may be configured to perform ECG measurements by measuring a voltage differential across an inner surface of the wearable ring device 104 (e.g., inner circumferential surface of the inner housing 805 that contacts the user's finger), and an outer surface of the wearable ring device 104 (e.g., outer circumferential surface of the outer housing 810 facing away from the user's finger).

In order to measure a voltage differential across the inner and outer surfaces, the wearable ring device 104 may be configured to conduct electrical current from the inner surface to the outer surface, and vice versa. In some aspects, this may be performed using dedicated electrodes, using components of the ring that exhibit electrical conductive properties, or both. For example, in some implementations, wearable ring device 104 may include dedicated electrodes 815 disposed within the inner surface and the outer surface of the wearable ring device 104, where the dedicated electrodes are electrically coupled to one another in order to measure a voltage differential across the electrodes. In this example, the electrodes may include conductive metal plates, such as conductive metal plates made of copper, titanium, stainless steel, steel, or other conductive materials.

In additional or alternative implementations, the inner housing may include, or may be made of, a conductive metal frame 820, such as titanium, stainless steel, or steel. In such cases, the conductive metal frame 820 may be electrically coupled to the electrode 815 on the outer surface of the wearable ring device 104 in order to measure a voltage differential across the inner and outer surfaces. In other words, the conductive metal frame 820 may serve as an additional electrode on the inner surface of the wearable ring device 104. For instance, a PCB that includes the respective components and sensors of the wearable ring device 104 that is disposed within the wearable ring device 104 may be coupled to the conductive metal frame 820 of the inner housing in one or more selected locations. Further, the electrode 815 on the outer surface may be electrically coupled to the PCB (and therefore the conductive metal frame 820) during the assembly process, such as through a soldering process.

In cases where the wearable ring device 104 includes an electrode 815 (e.g., conductive plate) on the outer surface of the wearable ring device 104, the outer housing 810 may include a non-conductive material or coating, such as a polyurethane (PUR) coating. In such cases, the electrode 815 may be embedded within the PUR surface, but may need to be visible and able to contact a user's skin in order to perform ECG measurements. In other words, the PUR coating may not be disposed over the electrode 815. For instance, in some cases, the PUR coating may be applied over the entire outer surface of the wearable ring device 104 (including the electrode 815), and the portion of the PUR coating disposed over the electrode 815 may subsequently be removed, such as though heat, manual removal (e.g., sanding, grinding), and the like. In some cases, additional decorative and/or conductive metal plates (e.g., electrodes) may be attached to the base metal of the wearable ring device 104 that is electrically coupled to the PCB, and therefore the conductive metal frame 820. In other words, in some implementations, the wearable ring device 104 may include multiple electrodes 815 on the outer surface that are configured to facilitate ECG measurements.

In order to perform ECG measurements, the conductive metal frame 820 (and/or an electrode 815 on the inner surface) may contact the user's finger, and the electrode 815 on the outer surface of the wearable ring device 104 may be pressed against the user's chest or another part of their body (e.g., the user's other hand) in order to close the circuit to record ECG measurements. As noted previously herein with respect to FIG. 7, in some implementations, the application page 705-*b* of the GUI 700 may display instructions and/or illustrations that instruct the user how to perform ECG measurements using the wearable ring device 104.

In order to facilitate efficient ECG measurements, the user may place the electrode 815 on the outer surface of the wearable ring device 104 on their chest. In such cases, the electrode 815 on the outer surface may be disposed on the outer surface on the palm-side of the wearable ring device 104 to enable the user to easily and naturally place the electrode against their chest.

Figure 9:
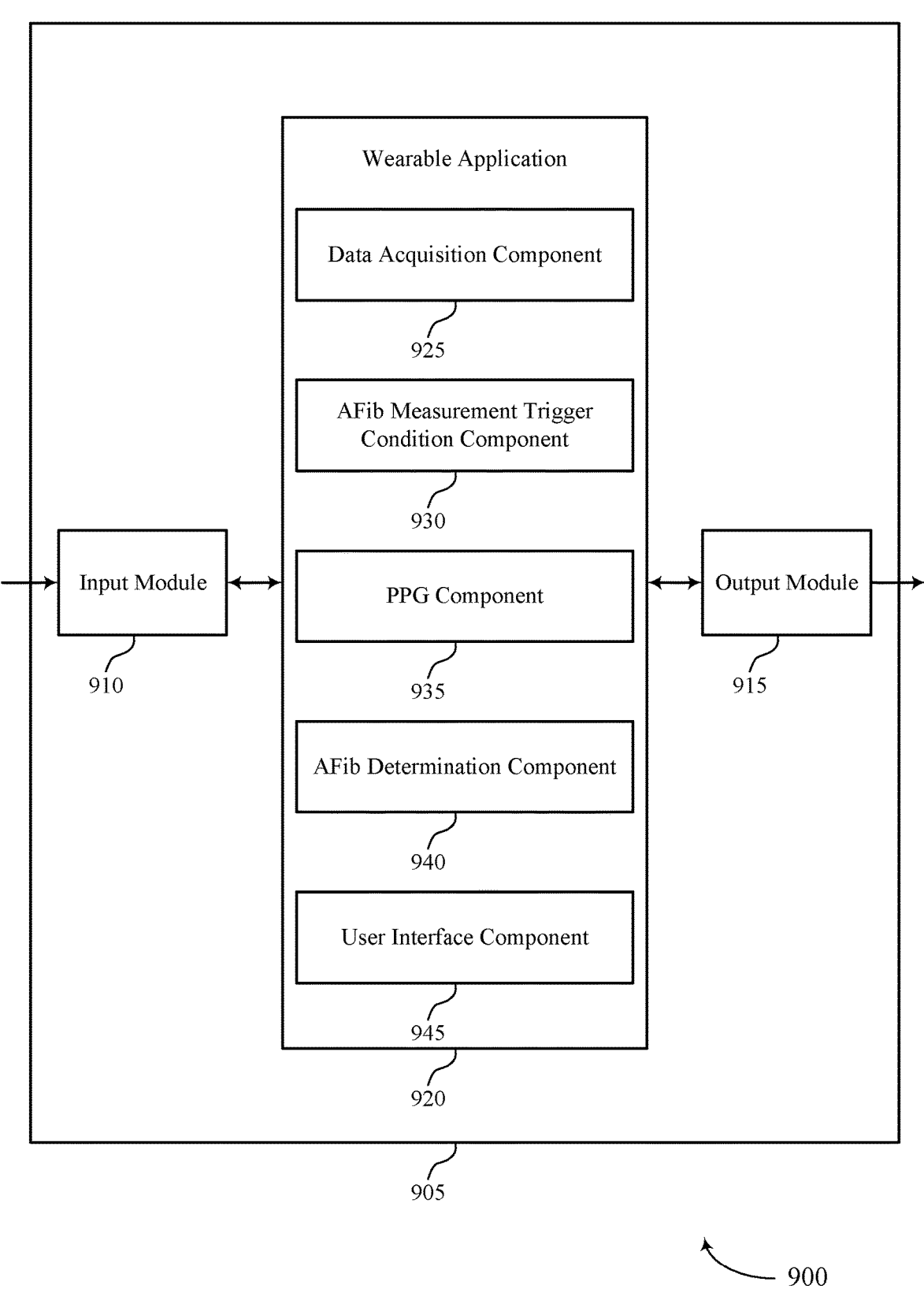
FIG. 9 shows a block diagram of an apparatus that supports techniques for detecting AFib in accordance with aspects of the present disclosure.

FIG. 9 shows a block diagram 900 of a device 905 that supports techniques for detecting AFib in accordance with aspects of the present disclosure. The device 905 may include an input module 910, an output module 915, and a wearable application 920. The device 905 may also include a processor. Each of these components may be in communication with one another (e.g., via one or more buses).

The input module 910 may provide a means for receiving information such as packets, user data, control information, or any combination thereof associated with various information channels (e.g., control channels, data channels, information channels related to illness detection techniques). Information may be passed on to other components of the device 905. The input module 910 may utilize a single antenna or a set of multiple antennas.

The output module 915 may provide a means for transmitting signals generated by other components of the device 905. For example, the output module 915 may transmit information such as packets, user data, control information, or any combination thereof associated with various information channels (e.g., control channels, data channels, information channels related to illness detection techniques). In some examples, the output module 915 may be co-located with the input module 910 in a transceiver module. The output module 915 may utilize a single antenna or a set of multiple antennas.

For example, the wearable application 920 may include a data acquisition component 925, an AFib measurement trigger condition component 930, a PPG component 935, an AFib determination component 940, a user interface component 945, or any combination thereof. In some examples, the wearable application 920, or various components thereof, may be configured to perform various operations (e.g., receiving, monitoring, transmitting) using or otherwise in cooperation with the input module 910, the output module 915, or both. For example, the wearable application 920 may receive information from the input module 910, send information to the output module 915, or be integrated in combination with the input module 910, the output module 915, or both to receive information, transmit information, or perform various other operations as described herein.

The data acquisition component 925 may be configured as or otherwise support a means for acquiring physiological data collected from a user via a wearable ring device, the physiological data comprising temperature data and motion data. The AFib measurement trigger condition component 930 may be configured as or otherwise support a means for identifying that a measurement trigger condition for AFib has been satisfied based at least in part on the temperature data satisfying a temperature threshold and the motion data satisfying a motion threshold. The PPG component 935 may be configured as or otherwise support a means for sampling PPG data for the user via the wearable ring device based at least in part on identifying satisfaction of the measurement trigger condition. The AFib determination component 940 may be configured as or otherwise support a means for classifying one or more AFib states based at least in part on the sampled PPG data. The user interface component 945 may be configured as or otherwise support a means for causing a GUI of a user device to display an indication of the one or more AFib states.

Figure 10:
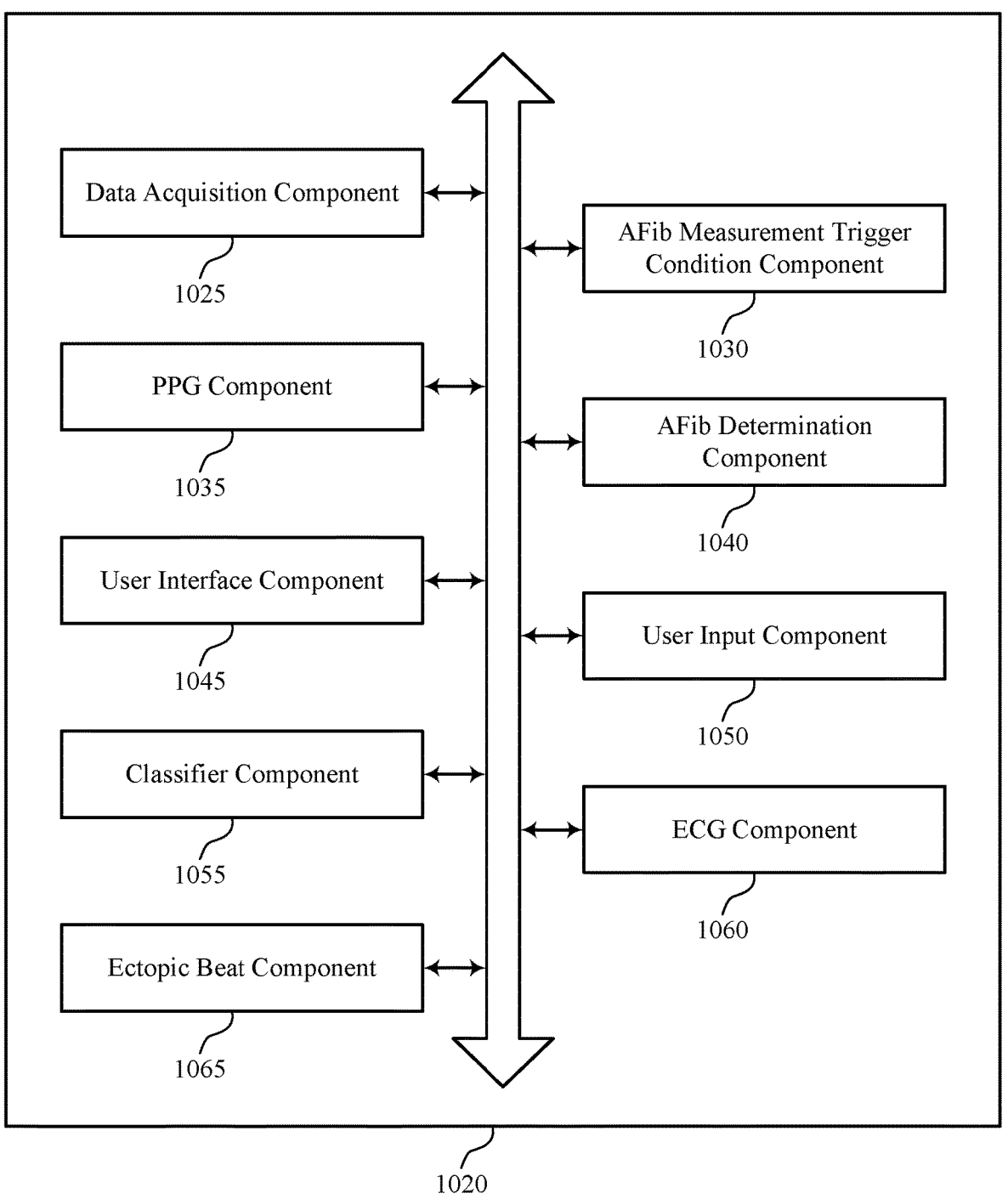
FIG. 10 shows a block diagram of a wearable application that supports techniques for detecting AFib in accordance with aspects of the present disclosure.

FIG. 10 shows a block diagram 1000 of a wearable application 1020 that supports techniques for detecting AFib in accordance with aspects of the present disclosure. The wearable application 1020 may be an example of aspects of a wearable application or a wearable application 920, or both, as described herein. The wearable application 1020, or various components thereof, may be an example of means for performing various aspects of techniques for detecting AFib as described herein. For example, the wearable application 1020 may include a data acquisition component 1025, an AFib measurement trigger condition component 1030, a PPG component 1035, an AFib determination component 1040, a user interface component 1045, a user input component 1050, a classifier component 1055, a ECG component 1060, an ectopic beat component 1065, or any combination thereof. Each of these components may communicate, directly or indirectly, with one another (e.g., via one or more buses).

The data acquisition component 1025 may be configured as or otherwise support a means for acquiring physiological data collected from a user via a wearable ring device, the physiological data comprising temperature data and motion data. The AFib measurement trigger condition component 1030 may be configured as or otherwise support a means for identifying that a measurement trigger condition for AFib has been satisfied based at least in part on the temperature data satisfying a temperature threshold and the motion data satisfying a motion threshold. The PPG component 1035 may be configured as or otherwise support a means for sampling PPG data for the user via the wearable ring device based at least in part on identifying satisfaction of the measurement trigger condition. The AFib determination component 1040 may be configured as or otherwise support a means for classifying one or more AFib states based at least in part on the sampled PPG data. The user interface component 1045 may be configured as or otherwise support a means for causing a GUI of a user device to display an indication of the one or more AFib states.

In some examples, the user input component 1050 may be configured as or otherwise support a means for receiving, via the user device, a user input comprising a request for an AFib measurement. In some examples, the AFib measurement trigger condition component 1030 may be configured as or otherwise support a means for evaluating the measurement trigger condition based at least in part on the user input, wherein identifying the satisfaction of the measurement trigger condition is based at least in part on the evaluating.

In some examples, the classifier component 1055 may be configured as or otherwise support a means for inputting the sampled PPG data into a classifier, wherein classifying the one or more AFib states is based at least in part on inputting the sampled PPG data into the classifier.

In some examples, the AFib measurement trigger condition component 1030 may be configured as or otherwise support a means for evaluating satisfaction of the measurement trigger condition in accordance with a regular periodicity, an irregular periodicity, or both, wherein identifying the satisfaction of the measurement trigger condition is based at least in part on the evaluating.

In some examples, the AFib determination component 1040 may be configured as or otherwise support a means for selectively adjusting one or more parameters associated with AFib measurement based at least in part on the one or more AFib states, the one or more parameters comprising a measurement periodicity, a power level associated with one or more sensors used to sample the PPG data, or both.

In some examples, the user input component 1050 may be configured as or otherwise support a means for receiving a user input to perform an ECG measurement based at least in part on the indication of the one or more AFib states. In some examples, the ECG component 1060 may be configured as or otherwise support a means for collecting ECG data for the user via the wearable ring device based at least in part on the user input. In some examples, the AFib determination component 1040 may be configured as or otherwise support a means for identifying one or more additional AFib states based at least in part on the collected ECG data. In some examples, the user interface component 1045 may be configured as or otherwise support a means for causing the GUI of a user device to display an indication of the one or more additional AFib states.

In some examples, the user interface component 1045 may be configured as or otherwise support a means for causing the GUI of the user device to display a prompt for performing the ECG measurement based at least in part on the one or more AFib states, wherein the user input is received in response to the prompt.

In some examples, the user interface component 1045 may be configured as or otherwise support a means for causing the GUI of the user device to display instructions for positioning the wearable ring device for the ECG measurement in response to receiving the user input, wherein collecting the ECG data is based at least in part on the instructions.

In some examples, to support collecting the ECG data, the ECG component 1060 may be configured as or otherwise support a means for measuring a voltage differential between an inner surface of the wearable ring device and an outer surface of the wearable ring device, wherein the ECG data is based at least in part on the voltage differential.

In some examples, the PPG component 1035 may be configured as or otherwise support a means for identifying a plurality of PPG pulses for the user based at least in part on the sampled PPG data. In some examples, the ectopic beat component 1065 may be configured as or otherwise support a means for identifying at least one ectopic beat associated with at least one PPG pulse of the plurality of PPG pulses based at least in part on one or more characteristics associated with the at least one PPG pulse, wherein classifying the one or more AFib states is based at least in part on identifying the at least one ectopic beat.

In some examples, the PPG component 1035 may be configured as or otherwise support a means for removing the at least one PPG pulse associated with the at least one ectopic beat from the plurality of PPG pulses to generate a reduced set of PPG pulses. In some examples, the AFib determination component 1040 may be configured as or otherwise support a means for identifying one or more irregular PPG pulses within the reduced set of PPG pulses based at least in part on the removing, wherein classifying the one or more AFib states is based at least in part on the one or more irregular PPG pulses.

In some examples, the ectopic beat component 1065 may be configured as or otherwise support a means for determining the one or more characteristics of the at least one ectopic beat based at least in part on a comparison of the at least one PPG pulse with a baseline PPG pulse.

In some examples, the one or more characteristics of the at least one PPG pulse comprises a timing of the at least one PPG pulse, an amplitude of the at least one PPG pulse, a time interval of the at least one PPG pulse, or any combination thereof.

In some examples, the PPG component 1035 may be configured as or otherwise support a means for identifying a plurality of PPG pulses for the user based at least in part on the sampled PPG data. In some examples, the PPG component 1035 may be configured as or otherwise support a means for comparing the plurality of PPG pulses for the user with a baseline PPG pulse for the user, wherein classifying the one or more AFib states is based at least in part on the comparison.

In some examples, the AFib measurement trigger condition component 1030 may be configured as or otherwise support a means for identifying satisfaction of the temperature threshold based at least in part on the temperature data being greater than or equal to the temperature threshold. In some examples, the AFib measurement trigger condition component 1030 may be configured as or otherwise support a means for identifying satisfaction of the motion threshold based at least in part on the motion data being less than or equal to the temperature threshold.

In some examples, the one or more AFib states comprises a positive AFib state, a negative AFib state, a potential AFib state, an inconclusive AFib state, or any combination thereof.

In some examples, the wearable device collects the physiological data from the user based on arterial blood flow.

Figure 11:
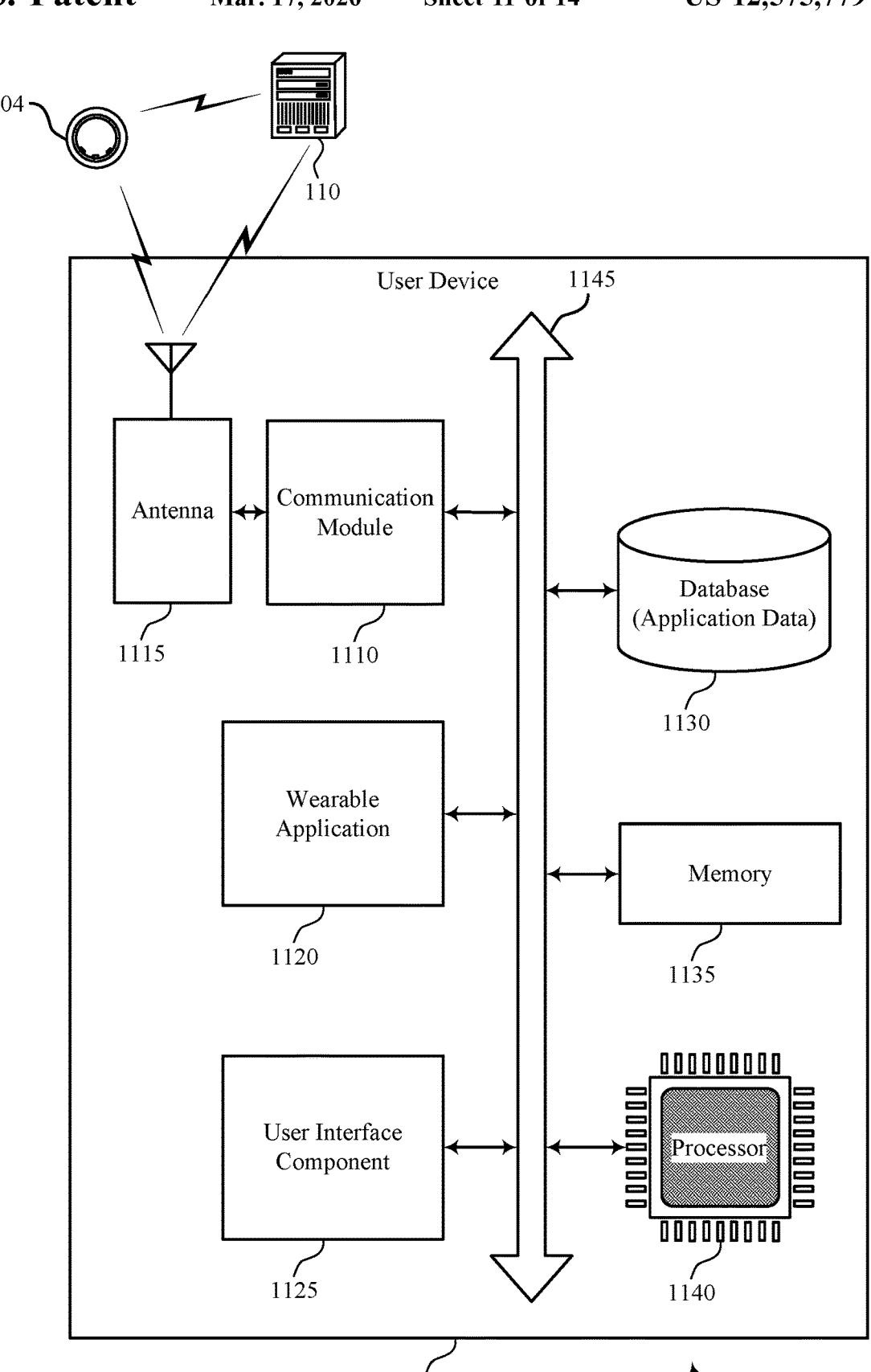
FIG. 11 shows a diagram of a system including a device that supports techniques for detecting AFib in accordance with aspects of the present disclosure.

FIG. 11 shows a diagram of a system 1100 including a device 1105 that supports techniques for detecting AFib in accordance with aspects of the present disclosure. The device 1105 may be an example of or include the compo-nents of a device 905 as described herein. The device 1105 may include an example of a user device 106, as described previously herein. The device 1105 may include components for bi-directional communications including components for transmitting and receiving communications with a wearable device 104 and a server 110, such as a wearable application 1120, a communication module 1110, an antenna 1115, a user interface component 1125, a database 1130 (e.g., appli-cation database), a memory 1135, and a processor 1140. These components may be in electronic communication or otherwise coupled (e.g., operatively, communicatively, func-tionally, electronically, electrically) via one or more buses (e.g., a bus 1145).

The communication module 1110 may manage input and output signals for the device 1105 via the antenna 1115. The communication module 1110 may include an example of the communication module 220-b of the user device 106 shown and described in FIG. 2. In this regard, the communication module 1110 may manage communications with the ring 104 and the server 110, as illustrated in FIG. 2. The communication module 1110 may also manage peripherals not integrated into the device 1105. In some cases, the communication module 1110 may represent a physical con-nection or port to an external peripheral. In some cases, the communication module 1110 may utilize an operating sys-tem such as iOS®, ANDROID®, MS-DOS®, MS-WIN-DOWS®, OS/2®, UNIX®, LINUX®, or another known operating system. In other cases, the communication module 1110 may represent or interact with a wearable device (e.g., ring 104), modem, a keyboard, a mouse, a touchscreen, or a similar device. In some cases, the communication module 1110 may be implemented as part of the processor 1140. In some examples, a user may interact with the device 1105 via the communication module 1110, user interface component 1125, or via hardware components controlled by the com-munication module 1110.

In some cases, the device 1105 may include a single antenna 1115. However, in some other cases, the device 1105 may have more than one antenna 1115 that may be capable of concurrently transmitting or receiving multiple wireless transmissions. The communication module 1110 may com-municate bi-directionally, via the one or more antennas 1115, wired, or wireless links as described herein. For example, the communication module 1110 may represent a wireless transceiver and may communicate bi-directionally with another wireless transceiver. The communication mod-ule 1110 may also include a modem to modulate the packets, to provide the modulated packets to one or more antennas 1115 for transmission, and to demodulate packets received from the one or more antennas 1115.

The user interface component 1125 may manage data storage and processing in a database 1130. In some cases, a user may interact with the user interface component 1125. In other cases, the user interface component 1125 may operate automatically without user interaction. The database 1130 may be an example of a single database, a distributed database, multiple distributed databases, a data store, a data lake, or an emergency backup database.

The memory 1135 may include RAM and ROM. The memory 1135 may store computer-readable, computer-ex-ecutable software including instructions that, when executed, cause the processor 1140 to perform various functions described herein. In some cases, the memory 1135 may contain, among other things, a BIOS that may control basic hardware or software operation such as the interaction with peripheral components or devices.

The processor 1140 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 1140 may be configured to operate a memory array using a memory controller. In other cases, a memory controller may be integrated into the processor 1140. The processor 1140 may be configured to execute computer-readable instructions stored in a memory 1135 to perform various functions (e.g., functions or tasks supporting a method and system for sleep staging algorithms).

For example, the wearable application 1120 may be configured as or otherwise support a means for acquiring physiological data collected from a user via a wearable ring device, the physiological data comprising temperature data and motion data. The wearable application 1120 may be configured as or otherwise support a means for identifying that a measurement trigger condition for AFib has been satisfied based at least in part on the temperature data satisfying a temperature threshold and the motion data satisfying a motion threshold. The wearable application 1120 may be configured as or otherwise support a means for sampling PPG data for the user via the wearable ring device based at least in part on identifying satisfaction of the measurement trigger condition. The wearable application 1120 may be configured as or otherwise support a means for classifying one or more AFib states based at least in part on the sampled PPG data. The wearable application 1120 may be configured as or otherwise support a means for causing a GUI of a user device to display an indication of the one or more AFib states.

By including or configuring the wearable application 1120 in accordance with examples as described herein, the device 1105 may support techniques for AFib prediction and detection. Moreover, aspects of the present disclosure may provide users with a more comprehensive picture into their overall health, including guidance regarding triggers for AFib episodes, and messaging that may enable users to make lifestyle changes to reduce a frequency or severity of AFib episodes.

The wearable application 1120 may include an application (e.g., "app"), program, software, or other component that is configured to facilitate communications with a ring 104, server 110, other user devices 106, and the like. For example, the wearable application 1120 may include an application executable on a user device 106 that is configured to receive data (e.g., physiological data) from a ring 104, perform processing operations on the received data, transmit and receive data with the servers 110, and cause presentation of data to a user 102.

FIG. 12 shows a flowchart illustrating a method 1200 that supports techniques for detecting AFib in accordance with aspects of the present disclosure. The operations of the method 1200 may be implemented by a user device or its components as described herein. For example, the operations of the method 1200 may be performed by a user device as described with reference to FIGS. 1 through 11. In some examples, a user device may execute a set of instructions to control the functional elements of the user device to perform the described functions. Additionally or alternatively, the user device may perform aspects of the described functions using special-purpose hardware.

At 1205, the method may include acquiring physiological data collected from a user via a wearable ring device, the physiological data comprising temperature data and motion data. The operations of 1205 may be performed in accordance with examples as disclosed herein. In some examples, aspects of the operations of 1205 may be performed by a data acquisition component 1025 as described with reference to FIG. 10.

At 1210, the method may include identifying that a measurement trigger condition for AFib has been satisfied based at least in part on the temperature data satisfying a temperature threshold and the motion data satisfying a motion threshold. The operations of 1210 may be performed in accordance with examples as disclosed herein. In some examples, aspects of the operations of 1210 may be performed by an AFib measurement trigger condition component 1030 as described with reference to FIG. 10.

At 1215, the method may include sampling PPG data for the user via the wearable ring device based at least in part on identifying satisfaction of the measurement trigger condition. The operations of 1215 may be performed in accordance with examples as disclosed herein. In some examples, aspects of the operations of 1215 may be performed by a PPG component 1035 as described with reference to FIG. 10.

At 1220, the method may include classifying one or more AFib states based at least in part on the sampled PPG data. The operations of 1220 may be performed in accordance with examples as disclosed herein. In some examples, aspects of the operations of 1220 may be performed by an AFib determination component 1040 as described with reference to FIG. 10.

At 1225, the method may include causing a GUI of a user device to display an indication of the one or more AFib states. The operations of 1225 may be performed in accordance with examples as disclosed herein. In some examples, aspects of the operations of 1225 may be performed by a user interface component 1045 as described with reference to FIG. 10.

Figure 13:
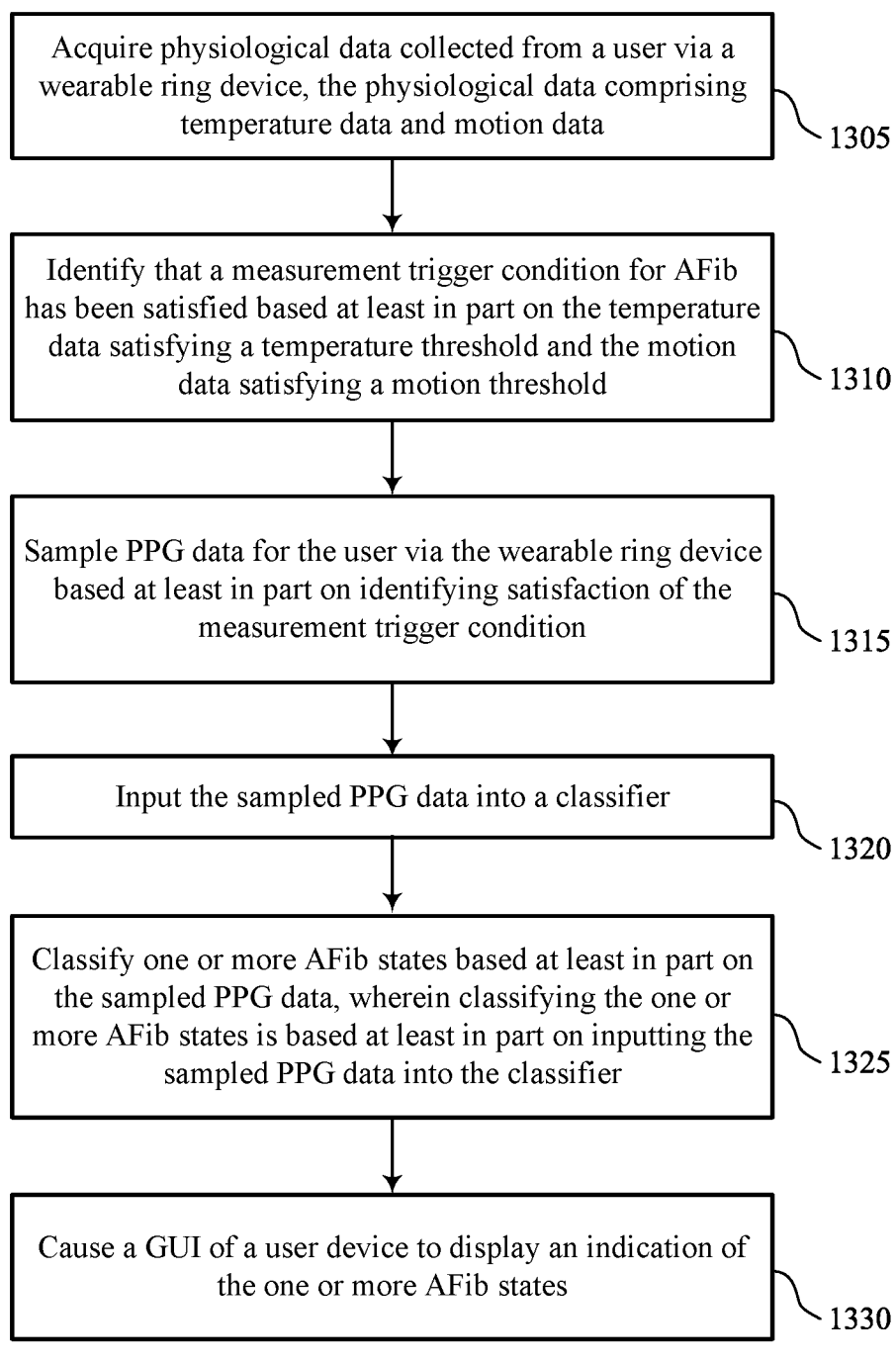

FIG. 13 shows a flowchart illustrating a method 1300 that supports techniques for detecting AFib in accordance with aspects of the present disclosure. The operations of the method 1300 may be implemented by a user device or its components as described herein. For example, the operations of the method 1300 may be performed by a user device as described with reference to FIGS. 1 through 11. In some examples, a user device may execute a set of instructions to control the functional elements of the user device to perform the described functions. Additionally or alternatively, the user device may perform aspects of the described functions using special-purpose hardware.

At 1305, the method may include acquiring physiological data collected from a user via a wearable ring device, the physiological data comprising temperature data and motion data. The operations of 1305 may be performed in accordance with examples as disclosed herein. In some examples, aspects of the operations of 1305 may be performed by a data acquisition component 1025 as described with reference to FIG. 10.

At 1310, the method may include identifying that a measurement trigger condition for AFib has been satisfied based at least in part on the temperature data satisfying a temperature threshold and the motion data satisfying a motion threshold. The operations of 1310 may be performed in accordance with examples as disclosed herein. In some examples, aspects of the operations of 1310 may be performed by an AFib measurement trigger condition component 1030 as described with reference to FIG. 10.

At 1315, the method may include sampling PPG data for the user via the wearable ring device based at least in part on identifying satisfaction of the measurement trigger condition. The operations of 1315 may be performed in accordance with examples as disclosed herein. In some examples, aspects of the operations of 1315 may be performed by a PPG component 1035 as described with reference to FIG. 10.

At 1320, the method may include inputting the sampled PPG data into a classifier, wherein classifying the one or more AFib states is based at least in part on inputting the sampled PPG data into the classifier. The operations of 1320 may be performed in accordance with examples as disclosed herein. In some examples, aspects of the operations of 1320 may be performed by a classifier component 1055 as described with reference to FIG. 10.

At 1325, the method may include classifying one or more AFib states based at least in part on the sampled PPG data. The operations of 1325 may be performed in accordance with examples as disclosed herein. In some examples, aspects of the operations of 1325 may be performed by an AFib determination component 1040 as described with reference to FIG. 10.

At 1330, the method may include causing a GUI of a user device to display an indication of the one or more AFib states. The operations of 1330 may be performed in accordance with examples as disclosed herein. In some examples, aspects of the operations of 1330 may be performed by a user interface component 1045 as described with reference to FIG. 10.

Figure 14:
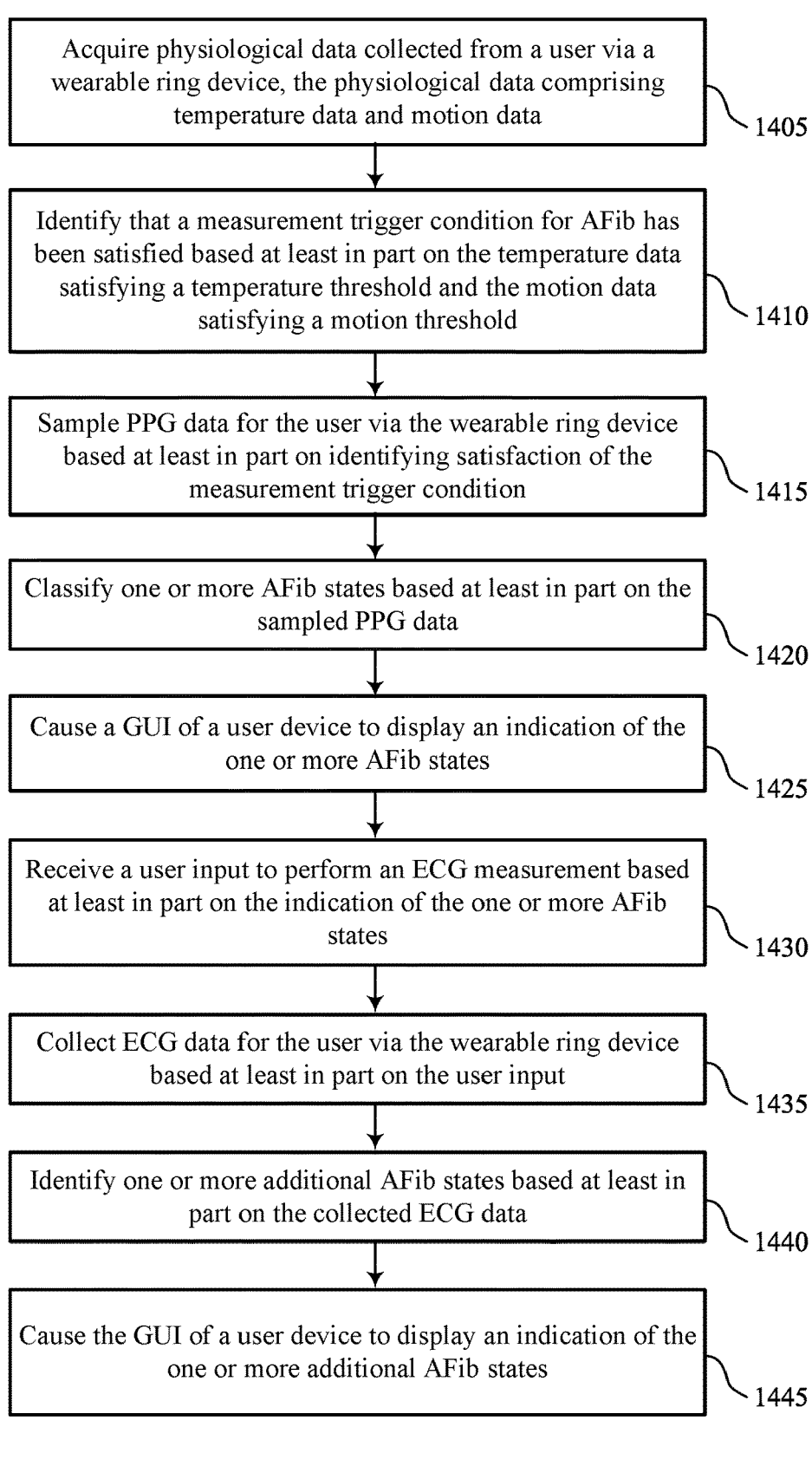

FIG. 14 shows a flowchart illustrating a method 1400 that supports techniques for detecting AFib in accordance with aspects of the present disclosure. The operations of the method 1400 may be implemented by a user device or its components as described herein. For example, the operations of the method 1400 may be performed by a user device as described with reference to FIGS. 1 through 11. In some examples, a user device may execute a set of instructions to control the functional elements of the user device to perform the described functions. Additionally or alternatively, the user device may perform aspects of the described functions using special-purpose hardware.

At 1405, the method may include acquiring physiological data collected from a user via a wearable ring device, the physiological data comprising temperature data and motion data. The operations of 1405 may be performed in accordance with examples as disclosed herein. In some examples, aspects of the operations of 1405 may be performed by a data acquisition component 1025 as described with reference to FIG. 10.

At 1410, the method may include identifying that a measurement trigger condition for AFib has been satisfied based at least in part on the temperature data satisfying a temperature threshold and the motion data satisfying a motion threshold. The operations of 1410 may be performed in accordance with examples as disclosed herein. In some examples, aspects of the operations of 1410 may be performed by an AFib measurement trigger condition component 1030 as described with reference to FIG. 10.

At 1415, the method may include sampling PPG data for the user via the wearable ring device based at least in part on identifying satisfaction of the measurement trigger condition. The operations of 1415 may be performed in accordance with examples as disclosed herein. In some examples, aspects of the operations of 1415 may be performed by a PPG component 1035 as described with reference to FIG. 10.

At 1420, the method may include classifying one or more AFib states based at least in part on the sampled PPG data.

The operations of 1420 may be performed in accordance with examples as disclosed herein. In some examples, aspects of the operations of 1420 may be performed by an AFib determination component 1040 as described with reference to FIG. 10.

At 1425, the method may include causing a GUI of a user device to display an indication of the one or more AFib states. The operations of 1425 may be performed in accordance with examples as disclosed herein. In some examples, aspects of the operations of 1425 may be performed by a user interface component 1045 as described with reference to FIG. 10.

At 1430, the method may include receiving a user input to perform an ECG measurement based at least in part on the indication of the one or more AFib states. The operations of 1430 may be performed in accordance with examples as disclosed herein. In some examples, aspects of the operations of 1430 may be performed by a user input component 1050 as described with reference to FIG. 10.

At 1435, the method may include collecting ECG data for the user via the wearable ring device based at least in part on the user input. The operations of 1435 may be performed in accordance with examples as disclosed herein. In some examples, aspects of the operations of 1435 may be performed by a ECG component 1060 as described with reference to FIG. 10.

At 1440, the method may include identifying one or more additional AFib states based at least in part on the collected ECG data. The operations of 1440 may be performed in accordance with examples as disclosed herein. In some examples, aspects of the operations of 1440 may be performed by an AFib determination component 1040 as described with reference to FIG. 10.

At 1445, the method may include causing the GUI of a user device to display an indication of the one or more additional AFib states. The operations of 1445 may be performed in accordance with examples as disclosed herein. In some examples, aspects of the operations of 1445 may be performed by a user interface component 1045 as described with reference to FIG. 10.

It should be noted that the methods described above describe possible implementations, and that the operations and the steps may be rearranged or otherwise modified and that other implementations are possible. Furthermore, aspects from two or more of the methods may be combined.

A method is described. The method may include acquiring physiological data collected from a user via a wearable ring device, the physiological data comprising temperature data and motion data, identifying that a measurement trigger condition for AFib has been satisfied based at least in part on the temperature data satisfying a temperature threshold and the motion data satisfying a motion threshold, sampling PPG data for the user via the wearable ring device based at least in part on identifying satisfaction of the measurement trigger condition, classifying one or more AFib states based at least in part on the sampled PPG data, and causing a GUI of a user device to display an indication of the one or more AFib states.

An apparatus is described. The apparatus may include a processor, memory coupled with the processor, and instructions stored in the memory. The instructions may be executable by the processor to cause the apparatus to acquire physiological data collected from a user via a wearable ring device, the physiological data comprising temperature data and motion data, identify that a measurement trigger condition for AFib has been satisfied based at least in part on the temperature data satisfying a temperature threshold and the motion data satisfying a motion threshold, sample PPG data for the user via the wearable ring device based at least in part on identifying satisfaction of the measurement trigger condition, classify one or more AFib states based at least in part on the sampled PPG data, and cause a GUI of a user device to display an indication of the one or more AFib states.

Another apparatus is described. The apparatus may include means for acquiring physiological data collected from a user via a wearable ring device, the physiological data comprising temperature data and motion data, means for identifying that a measurement trigger condition for AFib has been satisfied based at least in part on the temperature data satisfying a temperature threshold and the motion data satisfying a motion threshold, means for sampling PPG data for the user via the wearable ring device based at least in part on identifying satisfaction of the measurement trigger condition, means for classifying one or more AFib states based at least in part on the sampled PPG data, and means for causing a GUI of a user device to display an indication of the one or more AFib states.

A non-transitory computer-readable medium storing code is described. The code may include instructions executable by a processor to acquire physiological data collected from a user via a wearable ring device, the physiological data comprising temperature data and motion data, identify that a measurement trigger condition for AFib has been satisfied based at least in part on the temperature data satisfying a temperature threshold and the motion data satisfying a motion threshold, sample PPG data for the user via the wearable ring device based at least in part on identifying satisfaction of the measurement trigger condition, classify one or more AFib states based at least in part on the sampled PPG data, and cause a GUI of a user device to display an indication of the one or more AFib states.

Some examples of the method, apparatuses, and non-transitory computer-readable medium described herein may further include operations, features, means, or instructions for receiving, via the user device, a user input comprising a request for an AFib measurement and evaluating the measurement trigger condition based at least in part on the user input, wherein identifying the satisfaction of the measurement trigger condition may be based at least in part on the evaluating.

Some examples of the method, apparatuses, and non-transitory computer-readable medium described herein may further include operations, features, means, or instructions for inputting the sampled PPG data into a classifier, wherein classifying the one or more AFib states may be based at least in part on inputting the sampled PPG data into the classifier.

Some examples of the method, apparatuses, and non-transitory computer-readable medium described herein may further include operations, features, means, or instructions for evaluating satisfaction of the measurement trigger condition in accordance with a regular periodicity, an irregular periodicity, or both, wherein identifying the satisfaction of the measurement trigger condition may be based at least in part on the evaluating.

In some examples of the method, apparatuses, and non-transitory computer-readable medium described herein, selectively adjusting one or more parameters associated with AFib measurement based at least in part on the one or more AFib states, the one or more parameters comprising a measurement periodicity, a power level associated with one or more sensors used to sample the PPG data, or both.

Some examples of the method, apparatuses, and non-transitory computer-readable medium described herein may further include operations, features, means, or instructions for receiving a user input to perform an ECG measurement based at least in part on the indication of the one or more AFib states, collecting ECG data for the user via the wearable ring device based at least in part on the user input, identifying one or more additional AFib states based at least in part on the collected ECG data, and causing the GUI of a user device to display an indication of the one or more additional AFib states.

Some examples of the method, apparatuses, and non-transitory computer-readable medium described herein may further include operations, features, means, or instructions for causing the GUI of the user device to display a prompt for performing the ECG measurement based at least in part on the one or more AFib states, wherein the user input may be received in response to the prompt.

Some examples of the method, apparatuses, and non-transitory computer-readable medium described herein may further include operations, features, means, or instructions for causing the GUI of the user device to display instructions for positioning the wearable ring device for the ECG measurement in response to receiving the user input, wherein collecting the ECG data may be based at least in part on the instructions.

In some examples of the method, apparatuses, and non-transitory computer-readable medium described herein, collecting the ECG data may include operations, features, means, or instructions for measuring a voltage differential between an inner surface of the wearable ring device and an outer surface of the wearable ring device, wherein the ECG data may be based at least in part on the voltage differential.

Some examples of the method, apparatuses, and non-transitory computer-readable medium described herein may further include operations, features, means, or instructions for identifying a plurality of PPG pulses for the user based at least in part on the sampled PPG data and identifying at least one ectopic beat associated with at least one PPG pulse of the plurality of PPG pulses based at least in part on one or more characteristics associated with the at least one PPG pulse, wherein classifying the one or more AFib states may be based at least in part on identifying the at least one ectopic beat.

Some examples of the method, apparatuses, and non-transitory computer-readable medium described herein may further include operations, features, means, or instructions for removing the at least one PPG pulse associated with the at least one ectopic beat from the plurality of PPG pulses to generate a reduced set of PPG pulses and identifying one or more irregular PPG pulses within the reduced set of PPG pulses based at least in part on the removing, wherein classifying the one or more AFib states may be based at least in part on the one or more irregular PPG pulses.

Some examples of the method, apparatuses, and non-transitory computer-readable medium described herein may further include operations, features, means, or instructions for determining the one or more characteristics of the at least one ectopic beat based at least in part on a comparison of the at least one PPG pulse with a baseline PPG pulse.

In some examples of the method, apparatuses, and non-transitory computer-readable medium described herein, the one or more characteristics of the at least one PPG pulse comprises a timing of the at least one PPG pulse, an amplitude of the at least one PPG pulse, a time interval of the at least one PPG pulse, or any combination thereof.

Some examples of the method, apparatuses, and non-transitory computer-readable medium described herein may further include operations, features, means, or instructions for identifying a plurality of PPG pulses for the user based at least in part on the sampled PPG data and comparing the plurality of PPG pulses for the user with a baseline PPG pulse for the user, wherein classifying the one or more AFib states may be based at least in part on the comparison.

Some examples of the method, apparatuses, and non-transitory computer-readable medium described herein may further include operations, features, means, or instructions for identifying satisfaction of the temperature threshold based at least in part on the temperature data being greater than or equal to the temperature threshold and identifying satisfaction of the motion threshold based at least in part on the motion data being less than or equal to the temperature threshold.

In some examples of the method, apparatuses, and non-transitory computer-readable medium described herein, the one or more AFib states comprises a positive AFib state, a negative AFib state, a potential AFib state, an inconclusive AFib state, or any combination thereof.

In some examples of the method, apparatuses, and non-transitory computer-readable medium described herein, the wearable device collects the physiological data from the user based on arterial blood flow.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

45

What is claimed is:

1. A method for detecting physiological conditions associated with atrial fibrillation, comprising:

acquiring, via one or more sensors of a wearable ring device, physiological data from a user, the physiological data comprising temperature data and motion data, wherein the wearable ring device comprises:

a ring-shaped housing having an inner curved surface and an outer curved surface, wherein at least a portion of the inner curved surface is configured to contact a tissue of a finger of the user;

one or more temperature sensors arranged on the inner curved surface of the ring-shaped housing;

one or more photoplethysmogram (PPG) sensors arranged on the inner curved surface of the ring-shaped housing;

one or more processors disposed at least partially within the ring-shaped housing, the one or more processors electrically coupled with the one or more temperature sensors and the one or more PPG sensors, the one or more processors configured to generate physiological data associated with the user based at least in part on light received by the one or more PPG sensors;

a curved battery disposed at least partially within the ring-shaped housing, the curved battery electrically coupled with the one or more temperature sensors, the one or more PPG sensors, and the one or more processors; and a communication module electrically coupled with the one or more processors, the communication module configured to transmit the physiological data generated by the one or more processors;

identifying, by the one or more processors of the wearable ring device, that a measurement trigger condition for atrial fibrillation has been satisfied, wherein the measurement trigger condition is satisfied based on one or more values of the temperature data being above a temperature threshold and one or more values of the motion data being below a motion threshold;

supplying, by the one or more processors of the wearable ring device, a first power level to one or more PPG sensors of the wearable ring device based on the measurement trigger condition being satisfied, wherein the one or more PPG sensors emit light using the supplied first power level to sample PPG data of the user for one or more time periods;

inputting, to one or more first machine learning classifiers, a set of PPG pulses associated with the sampled PPG data;

classifying, by the one or more first machine learning classifiers, one or more atrial fibrillation states based at least in part on one or more characteristics of the set of PPG pulses, the one or more atrial fibrillation states indicative of a relative risk of atrial fibrillation occurrences for the user;

receiving, via a user device, an indication of one or more behaviors of the user associated with triggering of the atrial fibrillation occurrences;

predicting, by one or more second machine learning identifiers, one or more atrial fibrillation occurrences, wherein the one or more second machine learning identifiers are trained according to the indication of the one or more behaviors of the user; and causing a graphical user interface of the user device to display an indication of the one or more atrial fibrillation states, an indication of the one or more atrial fibrillation occurrences, or both.

2. The method of claim 1, further comprising:

receiving, via the user device, a user input comprising a request for an atrial fibrillation measurement; and evaluating the measurement trigger condition based at least in part on the user input, wherein identifying that the measurement trigger condition has been satisfied is based at least in part on the evaluating.

3. The method of claim 1, further comprising:

evaluating satisfaction of the measurement trigger condition in accordance with a regular periodicity, an irregular periodicity, or both, wherein identifying the satisfaction of the measurement trigger condition is based at least in part on the evaluating.

4. The method of claim 1, further comprising:

selectively adjusting one or more parameters associated with atrial fibrillation measurement based at least in part on the one or more atrial fibrillation states, the one or more parameters comprising a measurement periodicity, a power level supplied to the one or more PPG sensors, or both.

5. The method of claim 1, further comprising:

receiving a user input to perform an electrocardiogram (ECG) measurement based at least in part on the indication of the one or more atrial fibrillation states;

collecting ECG data for the user via the wearable ring device based at least in part on the user input;

identifying one or more additional atrial fibrillation states based at least in part on the collected ECG data; and causing the graphical user interface of the user device to display an indication of the one or more additional atrial fibrillation states.

6. The method of claim 5, further comprising:

causing the graphical user interface of the user device to display a prompt for performing the ECG measurement based at least in part on the one or more atrial fibrillation states, wherein the user input is received in response to the prompt.

7. The method of claim 5, further comprising:

causing the graphical user interface of the user device to display instructions for positioning the wearable ring device for the ECG measurement in response to receiving the user input, wherein collecting the ECG data is based at least in part on the instructions.

8. The method of claim 6, wherein collecting the ECG data comprises:

measuring a voltage differential between an inner surface of the wearable ring device and an outer surface of the wearable ring device, wherein the ECG data is based at least in part on the voltage differential.

9. The method of claim 1, further comprising:

identifying the set of PPG pulses for the user based at least in part on the sampled PPG data; and identifying at least one ectopic beat associated with at least one PPG pulse of the set of PPG pulses based at least in part on one or more characteristics associated with the at least one PPG pulse, wherein classifying the one or more atrial fibrillation states is based at least in part on identifying the at least one ectopic beat.

10. The method of claim 9, further comprising:

removing the at least one PPG pulse associated with the at least one ectopic beat from the set of PPG pulses; and identifying one or more irregular PPG pulses within a second set of PPG pulses based at least in part on the removing, wherein classifying the one or more atrial fibrillation states is based at least in part on the one or more irregular PPG pulses.

11. The method of claim 9, further comprising:
determining the one or more characteristics of the at least one ectopic beat based at least in part on a comparison of the at least one PPG pulse with a baseline PPG pulse.

12. The method of claim 9, wherein the one or more characteristics of the at least one PPG pulse comprises a timing of the at least one PPG pulse, an amplitude of the at least one PPG pulse, a time interval of the at least one PPG pulse, or any combination thereof.

13. The method of claim 1, further comprising:
identifying the set of PPG pulses for the user based at least in part on the sampled PPG data; and
comparing the set of PPG pulses for the user with a baseline PPG pulse for the user, wherein classifying the one or more atrial fibrillation states is based at least in part on the comparing.

14. The method of claim 1, wherein the one or more atrial fibrillation states comprises a positive atrial fibrillation state, a negative atrial fibrillation state, a potential atrial fibrillation state, an inconclusive atrial fibrillation state, or any combination thereof.

15. The method of claim 1, wherein the wearable ring device collects the physiological data from the user based on arterial blood flow.

16. The method of claim 1, further comprising:
causing the graphical user interface of the user device to display instructions for a user action in response to the one or more atrial fibrillation states, the one or more atrial fibrillation occurrences, or both.

17. The method of claim 16, wherein the user action is associated with a reduction in frequency, likelihood, severity, or any combination thereof, of the one or more atrial fibrillation occurrences.

18. A system, comprising:
a wearable ring device comprising a ring-shaped housing configured to be worn on a finger of a user, the wearable ring device comprising:
an inner curved surface and an outer curved surface, wherein at least a portion of the inner curved surface is configured to contact a tissue of the finger of the user;
one or more sensors configured to acquire physiological data from the user, the physiological data comprising temperature data and motion data, wherein the one or more sensors include one or more temperature sensors arranged on the inner curved surface of the ring-shaped housing and one or more photoplethysmogram PPG) sensors arranged on the inner curved surface of the ring-shaped housing; and
one or more processors disposed at least partially within the ring-shaped housing and electrically coupled with the one or more sensors, wherein the one or more processors are individually or collectively configured to:
generate physiological data associated with the user based at least in part on light received by the one or more PPG sensors;
identify that a measurement trigger condition for atrial fibrillation has been satisfied, wherein the measurement trigger condition is satisfied based on one or more values of the temperature data being above a temperature threshold and one or more values of the motion data being below a motion threshold; and supply a first power level to one or more PPG sensors of the wearable ring device based on the measurement trigger condition being satisfied, wherein the one or more PPG sensors emit light using the supplied first power level to sample PPG data of the user for one or more time periods;
a curved battery disposed at least partially within the ring-shaped housing, the curved battery electrically coupled with the one or more temperature sensors, the one or more PPG sensors, and the one or more processors;
a communication module electrically coupled with the one or more processors, the communication module configured to transmit the physiological data generated by the one or more processors;
a user device communicatively coupled with the wearable ring device; and
one or more additional processors communicatively coupled with the wearable ring device and the user device, wherein the one or more additional processors are individually or collectively configured to:
input, to one or more first machine learning classifiers, a set of PPG pulses associated with the sampled PPG data;
classify, by the one or more first machine learning classifiers, one or more atrial fibrillation states based at least in part on one or more characteristics of the set of PPG pulses, the one or more atrial fibrillation states indicative of a relative risk of atrial fibrillation occurrences for the user;
receive, from the user device, an indication of one or more behaviors of the user associated with triggering of the atrial fibrillation occurrences;
predict, by one or more second machine learning identifiers, one or more atrial fibrillation occurrences, wherein the one or more second machine learning identifiers are trained according to the indication of the one or more behaviors of the user; and
transmit a signal configured to cause a graphical user interface of the user device to display an indication of the one or more atrial fibrillation states, an indication of the one or more atrial fibrillation occurrences, or both.

19. The system of claim 18, wherein the one or more processors are further configured to:
receive, via the user device, a user input comprising a request for an atrial fibrillation measurement; and
evaluate the measurement trigger condition based at least in part on the user input, wherein identifying that the measurement trigger condition has been satisfied is based at least in part on the evaluating.

20. A non-transitory computer-readable medium storing code, the code comprising instructions executable by one or more processors to:
acquire, via one or more sensors of a wearable ring device, physiological data from a user, the physiological data comprising temperature data and motion data, wherein the wearable ring device comprises:
a ring-shaped housing having an inner curved surface and an outer curved surface, wherein at least a portion of the inner curved surface is configured to contact a tissue of a finger of the user;
one or more temperature sensors arranged on the inner curved surface of the ring-shaped housing;
one or more photoplethysmogram (PPG) sensors arranged on the inner curved surface of the ring-shaped housing;

one or more processors disposed at least partially within the ring-shaped housing, the one or more processors electrically coupled with the one or more temperature sensors and the one or more PPG sensors, the one or more processors configured to generate physiological data associated with the user based at least in part on light received by the one or more PPG sensors;

a curved battery disposed at least partially within the ring-shaped housing, the curved battery electrically coupled with the one or more temperature sensors, the one or more PPG sensors, and the one or more processors; and a communication module electrically coupled with the one or more processors, the communication module configured to transmit the physiological data generated by the one or more processors;

identify, by the one or more processors of the wearable ring device, that a measurement trigger condition for atrial fibrillation has been satisfied, wherein the measurement trigger condition is satisfied based on one or more values of the temperature data being above a temperature threshold and one or more values of the motion data being below a motion threshold;

supply, by the one or more processors, a first power level to one or more PPG sensors of the wearable ring device based on the measurement trigger condition being satisfied, wherein the one or more PPG sensors emit light using the supplied first power level to sample PPG data of the user for one or more time periods;

input, to one or more first machine learning classifiers, a set of PPG pulses associated with the sampled PPG data;

classify, by the one or more first machine learning classifiers, one or more atrial fibrillation states based at least in part on one or more characteristics of the set of PPG pulses, the one or more atrial fibrillation states indicative of a relative risk of atrial fibrillation occurrences for the user;

receive, via a user device, an indication of one or more behaviors of the user associated with triggering of the atrial fibrillation occurrences;

predict, by one or more second machine learning identifiers, one or more atrial fibrillation occurrences, wherein the one or more second machine learning identifiers are trained according to the indication of the one or more behaviors of the user; and cause a graphical user interface of the user device to display an indication of the one or more atrial fibrillation states, an indication of the one or more atrial fibrillation occurrences, or both.

* * * * *